United States Patent
Morisawa et al.

[11] 4,053,608
[45] Oct. 11, 1977

[54] COMPOSITIONS AND METHODS FOR THE TREATMENT OF COCCIDIOSIS

[75] Inventors: Yasuhiro Morisawa; Mitsuru Kataoka; Noritoshi Kitano; Toshiaki Matsuzawa, all of Tokyo, Japan

[73] Assignee: Sankyo Company Limited, Tokyo, Japan

[21] Appl. No.: 602,574

[22] Filed: Aug. 7, 1975

[30] Foreign Application Priority Data

| Aug. 14, 1974 | Japan | 49-93011 |
| Aug. 14, 1974 | Japan | 49-93012 |
| Aug. 24, 1974 | Japan | 49-97258 |
| Dec. 26, 1974 | Japan | 50-1695 |
| Jan. 11, 1975 | Japan | 50-5676 |
| Feb. 27, 1975 | Japan | 50-24207 |
| Mar. 12, 1975 | Japan | 50-29940 |
| Apr. 12, 1975 | Japan | 50-44518 |

[51] Int. Cl.² .................. A61K 31/455; A61K 31/44
[52] U.S. Cl. ..................................... 424/266; 424/263
[58] Field of Search ............................... 424/263, 266

[56] References Cited

PUBLICATIONS

Piskov et al. – Chem. Abst., vol. 76 (1972) p. 153,299y.
Aron-Samuel et al. – Chem. Abst., vol. 78 (1973) p. 4129g.
Nakadate et al. – Chem. Abst., vol. 62 (1965) p. 14620b.

*Primary Examiner*—Sam Rosen
*Attorney, Agent, or Firm*—Flynn & Frishauf

[57] ABSTRACT

Anticoccidial compositions which comprise as active ingredient pyridine derivatives having the formula

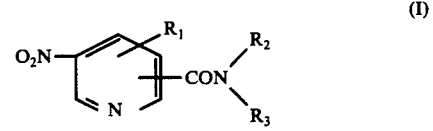

wherein
$R_1$ is hydrogen atom, a halomethyl group or methyl group;
$R_2$ is hydrogen atom or an alkyl group of 1–3 carbon atoms;
$R_3$ is hydrogen atom, an alkyl group of 1–3 carbon atoms, allyl group, an alkyl group having 2 or 3 carbon atoms and alkoxy of 1 or 2 carbon atoms as a substituent, an alkyl group having 1–3 carbon atoms and hydroxy as a substituent, an alkanoyl group of 1–18 carbon atoms, a haloacetyl group, an alkenoyl group of 3–11 carbon atoms, an aromatic acyl group, a heterocyclic acyl group, an N-alkyl-carbamoyl group of 1–4 carbon atoms in the alkyl moiety or hydroxy group;

provided that when $R_2$ is said alkyl group of 1–3 carbon atoms, $R_3$ is said alkyl group of 1–3 carbon atoms and inorganic acid addition salts thereof.

26 Claims, No Drawings

COMPOSITIONS AND METHODS FOR THE TREATMENT OF COCCIDIOSIS

This invention relates to novel compositions and methods for the treatment and prevention of the poultry disease coccidiosis.

More particularly, it is concerned with novel compositions containing, as an active anticoccidial agent, certain pyridinol derivatives.

Coccidiosis is a common and widespread disease of poultry, especially chickens and turkeys, and domestic animals such as rabbits, goats, sheep, and cattles, which disease is caused by a kind of protozoa belonging to class Sporozoa, order Coccidia, family Eimeriidae.

Coccidiosis of poultry and domestic animals is caused mainly by the protozoa belonging to genus Eimeria, which disease is classified to an acute type and a chronic one.

The former is caused by such species as $E.$ $tenella$ and $E.$ $necatrix$, and the characteristic feature of the disease is a copious bloody discharges from the ceca and small intestine of diseased poultries, which often die within a day or two.

The latter is caused by such species as $E.$ $acervulina$, $E.$ $maxima$, $E.$ $brunetti$, $E.$ $praecox$, $E.$ $hagani$, $E.$ $mitis$ and $E.$ $mivati$, and the characteristic feature of the disease is that the mortality of diseased poultries is rather few, whereas a poor weight gain, a reduced feed efficiency and a reduced efficiency of egg-production are commonly observed.

Infant rabbits as well as cattles, sheep and goats sometimes cause severe lesions by parasite Eimeria within their livers and intestines.

Oocysts of coccidia are excreted from an infected animal with feces, and spores having infectivity are produced within 24 – 48 hours under suitable conditions, which spores enter into a non-infected animal orally.

Oocysts grow at first asexually within the cells of the caecum or small intestine of the host animal, during which time the heaviest symptoms is observed. Then, they grow sexually and are excreted with the feces of the host animal and they exhibit an awful communicability.

The elimination or control of coccidiosis is, therefore, of paramount importance particularly in the poultry industry.

There have been proposed many preventive and curative methods for coccidiosis. One of them is a development is chemotherapeutic agents such as sulfa drugs, assenic compounds, nitrofuran derivatives, nitrophenide, Nicarbazine, Zoalane, pyrimidine derivatives (antithiamines), quinoline derivatives, guanidine derivatives, various antibiotics and so on.

But they have some defects; i.e. weak activity, narrow anti-protozoal spectrum, lack of security for animals or acquired resistance to the drugs by protozoa, respectively. Therefore, treatment with the hither-to-known anticoccidial agent is not satisfactory.

We have previously found that the pyridinol derivatives having the formula

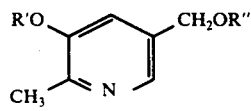

wherein R' and R" may be the same or different and each represents hydrogen atom, a lower alkyl group, an aralkyl group, an aliphatic, an aromatic or a heterocyclic acyl group, an alkoxycarbonyl group, an aralkoxycarbonyl group, an aryloxycarbonyl group; a N-substituted carbamoyl group, a N-substituted thiocarbamoyl group, a phosphono group show anticoccidial activities against species of the genus Eimeria, especially against $E.$ $acervulina$, as disclosed and claimed in our co-pending Japanese Patent Applications No. 105090/1972 and No. 41111/1973. As a result of our further extensive studies for anticoccidial agents, we have found that pyridine derivatives having the formula

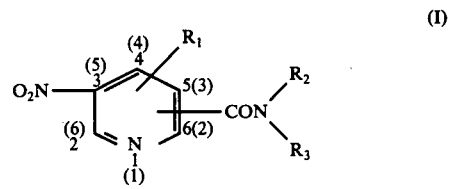

(I)

wherein
$R_1$ is hydrogen atom, a halomethyl group or methyl group;
$R_2$ is hydrogen atom or an alkyl group of 1–3 carbon atoms;
$R_3$ is hydrogen atom, an alkyl group of 1–3 carbon atoms, allyl group, an alkyl group having 2 or 3 carbon atoms and alkoxy of 1 or 2 carbon atoms as a substituent, an alkyl group having 1–3 carbon atoms and hydroxy as a substituent, an alkanoyl group of 1–18 carbon atoms, a haloacetyl group, an alkenoyl group of 3–11 carbon atoms, an aromatic acyl group, a heterocyclic acyl group, an N-alkylcarbamoyl group of 1–4 carbon atoms in the alkyl moiety or hydroxy group;

provided that when $R_2$ is said alkyl group of 1–3 carbon atoms, $R_3$ is said alkyl group of 1–3 carbon atoms and inorganic acid addition salts thereof, show a prominent anticoccidial activity against all species of the genus Eimeria, especially against $Eimeria$ $tenella$, which is known most pathogenic and lives in the caecum of host, and also they are highly effective against those strains resistant to known various thiamine type anticoccidial agents widely utilized in the art.

It is, accordingly, a primary object of this invention to provide an anticoccidial composition which are highly effective in treating and preventing coccidiosis.

Another objects will become apparent from the following detailed description of this invention.

According to this invention, there is provided an anticoccidial composition which comprises as an active ingredient the pyridine derivatives of the formula (I) or inorganic acid addition salts thereof intimately dispersed in or admixed with an inert carrier.

In the above formula (I), $R_1$ may be exemplified by hydrogen atom, chloromethyl, bromomethyl, dichloromethyl, dibromomethyl or methyl group. $R_2$ may be exemplified by hydrogen atom, methyl, ethyl, n-propyl or isopropyl group. $R_3$ may be exemplified by hydrogen atom, methyl, ethyl, n-propyl, isopropyl, allyl, 2-methoxyethyl, 2-ethoxyethyl, 3-methoxypropyl, hydroxymethyl, 2-hydroxyethyl, 2-hydroxypropyl, 3-hydroxypropyl, formyl, acetyl, propionyl, butyryl, isobutyryl, valeryl, isovaleryl, 2-methylbutyryl, pivaloyl, hexanoyl, 2-methyl-n-valeryl, 3-methyl-n-valeryl, 4-methyl-n-valeryl, 2-ethyl-n-butyryl, heptanoyl, octanoyl, 2-ethylhexanoyl, nonanoyl, 3,3,5-trimethylhexanoyl, decanoyl, undecanoyl, n-lauroyl, myristoyl, pentadecanoyl, palmitoyl, stearoyl, acryloyl, crotonoyl, 3-butenoyl, methacryloyl, tigloyl, sorboyl, 10-undecenoyl, oleoyl, chloroacetyl, bromoacetyl, benzoyl, 2,3-dimethoxybenzoyl, 3,4-dimethoxybenzoyl, 3,5-dimethylbenzoyl, 0-, m-, p-toluoyl, o-, m-, p-chlorobenzoyl, o-, m-, p-bromobenzoyl, p-methoxybenzoyl, o-, m-, p-acetylaminobenzoyl, o-, m-, p-cyanobenzoyl, 2-ethoxy-4-acetylaminobenzoyl, 2-ethoxy-4-dimethylaminobenzoyl, 2-methoxy-4-acetylaminobenzoyl, 2-furoyl, 2-thenoyl, isonicotinoyl, nicotinoyl, 5-nitronicotinoyl, 2-methyl-5-nitronicotinoyl, N-methylcarbamoyl, N-ethylcarbamoyl, N-n-propylcarbamoyl, N-isopropylcarbamoyl, N-n-butylcarbamoyl, N-isobutylcarbamoyl, N-t-butylcarbamoyl or hydroxy group.

Further, the compound of the formula (I) wherein, $NO_2$ is at the 3-position of the pyridine ring $R_1$ is a methyl group at the 6-position of the pyridine ring, $R_2$ and $R_3$ are hydrogen atom and the

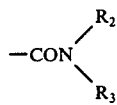

group is attached to the pyridine ring at the 5-position thereof is disclosed as such in "Journal of Organic Chemistry" (Zhurnal. Organich. Khimii, Russian origin, Vol. 6, 559, 1970). However, it should be noted that this compound is clearly disclosed therein to show no anticoccidial activity.

Among the pyridine compounds of the formula (I) which may be employed in this invention, as a preferable group may be mentioned those pyridine compounds of the formula (I)
wherein
$R_2$ is hydrogen atom or an alkyl group of 1 or 2 carbon atoms;
$R_3$ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, as alkanoyl group of 1-9 carbon atoms, chloroacetyl group, an alkenoyl group of 3 or 4 carbon atoms, a benzoyl group which may be substituted with methyl, methoxy or halogen, nicotinoyl group, 5-nitronicotinoyl group, 2-thenoyl group, an N-alkylcarbamoyl group of 1 or 2 carbon atoms in the alkyl moiety or hydroxy group;
provided that when $R_2$ is said alkyl group, $R_3$ is said alkyl group of 1 or 2 carbon atoms, in view of their anticoccidial activities.

More preferable group of the pyridine compounds of the formula (I) involves the following four groups A, B, C and D.

Group A . . . those pyridine compounds of the formula (I) wherein $R_1$ is attached to the pyridine ring at the 6-position thereof and is hydrogen atom or methyl group, the

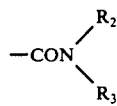

group is attached to the pyridine ring at the 5-position thereof and $R_2$ is hydrogen atom or an alkyl group of 1 or 2 carbon atoms; $R_3$ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1-9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group; provided that when $R_2$ is said alkyl group, $R_3$ is said alkyl group of 1 or 2 carbon atoms.

Group B . . . those pyridine compounds of the formula (I) wherein $R_1$ is attached to the pyridine ring at the 2-position thereof and is hydrogen atom or methyl group, the

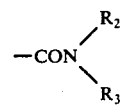

group is attached to the pyridine ring at the 4-position thereof and $R_2$ and $R_3$ are as defined above with respect to the Group A.

Group C . . . those pyridine compounds of the formula (I) wherein $R_1$ is hydrogen atom or methyl group, the

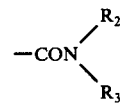

group is attached to the pyridine ring at the 2-position thereof and $R_2$ and $R_3$ are as defined above with respect to the Group A.

Group D . . . those pyridine compounds of the formula (I) wherein $R_1$ is attached to the pyridine ring at the 2- or 4-position thereof and is hydrogen atom or methyl group, the

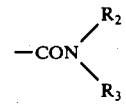

group is attached to the pyridine ring at the 6-position thereof and $R_2$ and $R_3$ are as defined above with respect to the Group A.

Among the Groups A, B, C and D, there may be preferably mentioned the Groups A, B and C, in particular the Groups A and B, in view of their anticoccidial activities.

The inorganic acid addition salts of the pyridine compounds of the formula (I) also show an anticoccidialactivity.

There is no limitation to the inorganic acid so far as salts formed are pharmaceutically acceptable and nontoxic to animals.

Suitable salts of this invention are as follows: Acid addition salts in which an acid is such inorganic acid as hydrochloric acid, sulfuric acid, nitric acid or phosphonic acid.

Of the pyridine derivatives of the formula (I), representative examples thereof are listed below, but they are not intended to be limiting the scope of this invention.

| Compound No. | Chemical Name |
|---|---|
| (1) | 5-Nitronicotinamide |
| (2) | N-Methyl 5-Nitronicotinamide |
| (3) | N-Ethyl 5-Nitronicotinamide |
| (4) | N-n-Propyl 5-Nitronicotinamide |
| (5) | N-i-Propyl 5-Nitronicotinamide |
| (6) | N-n-Butyl 5-Nitronicotinamide |
| (7) | N-i-Butyl 5-Nitronicotinamide |
| (8) | N-sec-Butyl 5-Nitronicotinamide |
| (9) | N-Hydroxymethyl 5-Nitronicotinamide |
| (10) | N-(2-Hydroxyethyl) 5-Nitronicotinamide |
| (11) | N-(3-hydroxypropyl) 5-Nitronicotinamide |
| (12) | N-(2-Methoxyethyl) 5-Nitronicotinamide |
| (13) | N-(2-ethoxyethyl) 5-Nitronicotinamide |
| (14) | N-(3-Methoxypropyl) 5-Nitronicotinamide |
| (15) | N-Allyl 5-Nitronicotinamide |
| (16) | N,N-Dimethyl 5-Nitronicotinamide |
| (17) | N,N-Diethyl 5-Nitronicotinamide |
| (18) | N,N-Di-n-propyl 5-Nitronicotinamide |
| (19) | N,N-Di-i-propyl 5-Nitronicotinamide |
| (20) | N-Ethyl-N-methyl 5-Nitronicotinamide |
| (21) | N-Methyl-N-propyl 5-Nitronicotinamide |
| (22) | N-Ethyl-N-propyl 5-Nitronicotinamide |
| (23) | N-(2-Ethoxyethyl)-N-methyl 5-Nitronicotinamide |
| (24) | N-(2-Methoxyethyl)-N-methyl 5-Nitronicotinamide |
| (25) | N-(2-Ethoxyethyl)-N-ethyl 5-Nitronicotinamide |
| (26) | N-(2-Methoxyethyl)-N-ethyl 5-Nitronicotinamide |
| (27) | N-Formyl 5-Nitronicotinamide |
| (28) | N-Acetyl 5-Nitronicotinamide |
| (29) | N-Propionyl 5-Nitronicotinamide |
| (30) | N-Butyryl 5-Nitronicotinamide |
| (31) | N-Isobutyryl 5-Nitronicotinamide |
| (32) | N-Valeryl 5-Nitronicotinamide |
| (33) | N-Isovaleryl 5-Nitronicotinamide |
| (34) | N-2-Methylbutyryl 5-Nitronicotinamide |
| (35) | N-Pivaloyl 5-Nitronicotinamide |
| (36) | N-Hexanoyl 5-Nitronicotinamide |
| (37) | N-Heptanoyl 5-Nitronicotinamide |
| (38) | N-Octanoyl 5-Nitronicotinamide |
| (39) | N-2-Ethylhexanoyl 5-Nitronicotinamide |
| (40) | N-Nonanoyl 5-Nitronicotinamide |
| (41) | N-3,5,5-Trimethylhexanoyl 5-Nitronicotinamide |
| (42) | N-Decanoyl 5-Nitronicotinamide |
| (43) | N-Lauroyl 5-Nitronicotinamide |
| (44) | N-Myristoyl 5-Nitronicotinamide |
| (45) | N-Palmitoyl 5-Nitronicotinamide |
| (46) | N-Stearoyl 5-Nitronicotinamide |
| (47) | N-Acryloyl 5-Nitronicotinamide |
| (48) | N-Crotonoyl 5-Nitronicotinamide |
| (49) | N-3-Butenoyl 5-Nitronicotinamide |
| (50) | N-Methacryloyl 5-Nitronicotinamide |
| (51) | N-Tigloyl 5-Nitronicotinamide |
| (52) | N-Sorboyl 5-Nitronicotinamide |
| (53) | N-Benzoyl 5-Nitronicotinamide |
| (54) | N-(2,3-Dimethoxybenzoyl) 5-Nitronicotinamide |
| (55) | N-(3,4-Dimethoxybenzoyl) 5-Nitronicotinamide |
| (56) | N-(o-Toluoyl) 5-Nitronicotinamide |
| (57) | N-(m-Toluoyl) 5-Nitronicotinamide |
| (58) | N-(p-Toluoyl) 5-Nitronicotinamide |
| (59) | N-(3,5-Dimethylbenzoyl 5-Nitronicotinamide |
| (60) | N-(o-Chlorobenzoyl) 5-Nitronicotinamide |
| (61) | N-(m-Chlorobenzoyl) 5-Nitronicotinamide |
| (62) | N-(p-Chlorobenzoyl) 5-Nitronicotinamide |
| (63) | N-(m-Bromobenzoyl) 5-Nitronicotinamide |
| (64) | N-(p-Bromobenzoyl) 5-Nitronicotinamide |
| (65) | N-(p-Methoxybenzoyl) 5-Nitronicotinamide |
| (66) | N-(m-Acetylaminobenzoyl) 5-Nitronicotinamide |
| (67) | N-(p-Acetylaminobenzoyl) 5-Nitronicotinamide |
| (68) | N-(p-Cyanobenzoyl 5-Nitronicotinamide |
| (69) | N-(2-Ethoxy-4-acetylaminobenzoyl) 5-Nitronicotinamide |
| (70) | N-(2-Furoyl) 5-Nitronicotinamide |
| (71) | N-(2-Thenoyl) 5-Nitronicotinamide |
| (72) | N-Isonicotinoyl 5-Nitronicotinamide |
| (73) | N-Nicotinoyl 5-Nitronicotinamide |
| (74) | N-(5-Nitronicotinoyl) 5-Nitronicotinamide |
| (75) | 3-(4-Methylallophanoyl)-5-Nitropyridine |
| (76) | 3-(4-Ethylallophanoyl)-5-nitropyridine |
| (77) | 3-(4-Isopropylallophanoyl)-5-nitropyridine |
| (78) | 5-Nitro-3-(4-n-propylallophanoyl)pyridine |
| (79) | 3-(4-n-Butylallophanoyl)-5-nitropyridine |
| (80) | 5-Nitronicotinohydroxamic acid |
| (81) | 3-(4-Isobutylallophanoyl)-5-nitropyridine |
| (82) | 2-Methyl-5-nitronicotinamide |
| (83) | N-Methyl 2-Methyl-5-nitronicotinamide |
| (84) | N-Ethyl 2-Methyl-5-nitronicotinamide |
| (85) | N-n-Propyl 2-Methyl-5-nitronicotinamide |
| (86) | N-i-Propyl 2-Methyl-5-nitronicotinamide |
| (87) | N-n-Butyl 2-Methyl-5-nitronicotinamide |
| (88) | N-i-Butyl 2-Methyl-5-nitronicotinamide |
| (89) | N-sec-Butyl 2-Methyl-5-nitronicotinamide |
| (90) | N-hydroxymethyl 2-Methyl-5-nitronicotinamide |
| (91) | N-(2-Hydroxyethyl) 2-Methyl-5-nitronicotinamide |
| (92) | N-(3-Hydroxypropyl) 2-Methyl-5-nitronicotinamide |
| (93) | N-(2-Methoxyethyl) 2-Methyl-5-nitronicotinamide |
| (94) | N-(2-Ethoxyethyl) 2-Methyl-5-nitronicotinamide |
| (95) | N-(3-Methoxypropyl) 2-Methyl-5-nitronicotinamide |
| (96) | N-Allyl 2-Methyl-5-nitronicotinamide |
| (97) | N,N-Dimethyl 2-Methyl-5-nitronicotinamide |
| (98) | N,N-Diethyl 2-Methyl-5-nitronicotinamide |
| (99) | N,N-Diisopropyl 2-Methyl-5-nitronicotinamide |
| (100) | N,N-Di-n-propyl 2-Methyl-5-nitronicotinamide |
| (101) | N-Ethyl-N-methyl 2-Methyl-5-nitronicotinamide |
| (102) | N-Methyl-N-propyl 2-Methyl-5-nitronicotinamide |
| (103) | N-Ethyl-N-propyl 2-Methyl-5-nitronicotinamide |
| (104) | N-(2-Ethoxyethyl)-N-methyl 2-Methyl-5-nitronicotinamide |
| (105) | N-(2-Methoxyethyl)-N-methyl 2-Methyl-5-nitronicotinamide |
| (106) | N-(2-Ethoxyethyl)-N-ethyl 2-Methyl-5-nitronicotinamide |
| (107) | N-(2-Methoxyethyl)-N-ethyl 2-Methyl-5-nitronicotinamide |
| (108) | N-Formyl 2-Methyl-5-nitronicotinamide |
| (109) | N-Acetyl 2-Methyl-5-nitronicotinamide |
| (110) | N-Propionyl 2-Methyl-5-nitronicotinamide |
| (111) | N-Butyryl 2-Methyl-5-nitronicotinamide |
| (112) | N-Isobutyryl 2-Methyl-5-nitronicotinamide |
| (113) | N-Valeryl 2-Methyl-5-nitronicotinamide |
| (114) | N-Isovaleryl 2-Methyl-5-nitronicotinamide |
| (115) | N-2-Methylbutyryl 2-Methyl-5-nitronicotinamide |
| (116) | N-Pivaloyl 2-Methyl-5-nitronicotinamide |
| (117) | N-Hexanoyl 2-Methyl-5-nitronicotinamide |
| (118) | N-Heptanoyl 2-Methyl-5-nitronicotinamide |
| (119) | N-Octanoyl 2-Methyl-5-nitronicotinamide |
| (120) | N-2-Ethylhexanoyl 2-Methyl-5-nitronicotinamide |
| (121) | N-Nonanoyl 2-Methyl-5-nitronicotinamide |
| (122) | N-3,5,5-Trimethylhexanoyl 2-Methyl-5-nitronicotinamide |
| (123) | N-Decanoyl 2-Methyl-5-nitronicotinamide |
| (124) | N-Undecanoyl 2-Methyl-5-nitronicotinamide |
| (125) | N-Lauroyl 2-Methyl-5-nitronicotinamide |
| (126) | N-Myristoyl 2-Methyl-5-nitronicotinamide |
| (127) | N-Palmitoyl 2-Methyl-5-nitronicotinamide |
| (128) | N-Stearoyl 2-Methyl-5-nitronicotinamide |
| (129) | N-Acryloyl 2-Methyl-5-nitronicotinamide |
| (130) | N-Crotonoyl 2-Methyl-5-nitronicotinamide |
| (131) | N-3-Butenoyl 2-Methyl-5-nitronicotinamide |
| (132) | N-Methacryloyl 2-Methyl-5-nitronicotinamide |
| (133) | N-Tigloyl 2-Methyl-5-nitronicotinamide |
| (134) | N-Sorboyl 2-Methyl-5-nitronicotinamide |
| (135) | N-10-Undecanoyl 2-Methyl-5-nitronicotinamide |
| (136) | N-(3,5-Dimethylbenzoyl) 2-Methyl-5-nitronicotinamide |
| (137) | N-Benzoyl 2-Methyl-5-nitronicotinamide |
| (138) | N-(3,4-Dimethylbenzoyl) 2-Methyl-5-nitronicotinamide |
| (139) | N-(o-Toluoyl) 2-Methyl-5-nitronicotinamide |
| (140) | N-(m-Toluoyl) 2-Methyl-5-nitronicotinamide |
| (141) | N-(p-Toluoyl) 2-Methyl-5-nitronicotinamide |
| (142) | N-(o-Chlorobenzoyl) 2-Methyl-5-nitronicotinamide |
| (143) | N-(m-Chlorobenzoyl) 2-Methyl-5-nitronicotinamide |
| (144) | N-(p-Chlorobenzoyl) 2-Methyl-5-nitronicotinamide |
| (145) | N-(p-Bromobenzoyl) 2-Methyl-5-nitronicotinamide |
| (146) | N-(p-Methoxybenzoyl) 2-Methyl-5-nitronicotinamide |
| (147) | N-(p-Acetylaminobenzoyl) 2-Methyl-5-nitronicotinamide |
| (148) | N-(2-Ethoxy-4-acetylaminobenzoyl) 2-Methyl-5-nitronicotinamide |
| (149) | N-(2-Furoyl) 2-Methyl-5-nitronicotinamide |
| (150) | N-(2-Thenoyl) 2-Methyl-5-nitronicotinamide |
| (151) | N-Nicotinoyl 2-Methyl-5-nitronicotinamide |
| (152) | N-(5-Nitronicotinoyl) 2-Methyl-5-nitronicotinamide |
| (153) | 2-Methyl-3-(4-methylallophanoyl)-5-nitropyridine |
| (154) | 3-(4-Ethylallophanoyl)-2-methyl-5-nitropyridine |
| (155) | 2-Methyl-5-nitro-3-(4-n-propylallophanoyl)-pyridine |
| (156) | 3-(4-Isopropylallophanoyl)-2-methyl-5-nitropyridine |
| (157) | 3-(4-n-Butylallophanoyl)-2-methyl-5-nitropyridine |
| (158) | 3-(4-Isobutylallophanoyl)-2-methyl-5-nitronicotinamide |
| (159) | 2-Methyl-5-nitronicotinohydroxamic acid |
| (160) | Bromomethyl 5-nitronicotinamide |
| (161) | 2-Dibromomethyl-5-nitronicotinamide |
| (162) | 2-Chloromethyl-5-nitronicotinamide |

| Compound No. | Chemical Name |
|---|---|
| (163) | 2-Dichloromethyl-5-nitronicotinamide |
| (164) | N,N-Dimethyl 2-Bromomethyl-5-nitronicotinamide |
| (165) | N,N-Diethyl 2-Bromomethyl-5-nitronicotinamide |
| (166) | N,N-Dipropyl 2-Bromomethyl-5-nitronicotinamide |
| (167) | N-Ethyl-N-methyl 2-Bromomethyl-5-nitronicotinamide |
| (168) | N-Acetyl 2-Bromomethyl-5-nitronicotinamide |
| (169) | N,N-Dimethyl 2-Dibromomethyl-5-nitronicotinamide |
| (170) | N,N-Diethyl 2-Dibromomethyl-5-nitronicotinamide |
| (171) | N,N-Dipropyl 2-Dibromomethyl-5-nitronicotinamide |
| (172) | N-Ethyl-N-methyl 2-Dibromomethyl-5-nitronicotinamide |
| (173) | N-Acetyl 2-Dibromomethyl-5-nitronicotinamide |
| (174) | N-Propionyl 2-Dibromomethyl-5-nitronicotinamide |
| (175) | N-n-Butyryl 2-Dibromomethyl-5-nitronicotinamide |
| (176) | N-Isobutyryl 2-Bromomethyl-5-nitronicotinamide |
| (177) | N-Crotonoyl 2-Dibromomethyl-5-nitronicotinamide |
| (178) | N,N-Diethyl 2-Dichloromethyl-5-nitronicotinamide |
| (179) | N,N-Dipropyl 2-Dichloromethyl-5-nitronicotinamide |
| (180) | N-Ethyl-N-methyl 2-Dichloromethyl-5-nitronicotinamide |
| (181) | N-Acetyl 2-Dichloromethyl-5-nitronicotinamide |
| (182) | N-Propionyl 2-Dichloromethyl-5-nitronicotinamide |
| (183) | N-n-Butyryl 2-Dichloromethyl-5-nitronicotinamide |
| (184) | N-Crotonoyl 2-Dichloromethyl-5-nitronicotinamide |
| (185) | 3-Nitroisonicotinamide |
| (186) | N-Methyl 3-Nitroisonicotinamide |
| (187) | N-Ethyl 3-Nitroisonicotinamide |
| (188) | N-Propyl 3-Nitroisonicotinamide |
| (189) | N,N-Dimethyl 3-Nitroisonicotinamide |
| (190) | N,N-Diethyl 3-Nitroisonicotinamide |
| (191) | N-Ethyl-N-methyl 3-Nitroisonicotinamide |
| (192) | N-Allyl 3-Nitroisonicotinamide |
| (193) | N-Hydroxymethyl 3-Nitroisonicotinamide |
| (194) | N-Acetyl 3-Nitroisonicotinamide |
| (195) | N-Propionyl 3-Nitroisonicotinamide |
| (196) | N-Formyl 3-Nitroisonicotinamide |
| (197) | N-Butyryl 3-Nitroisonicotinamide |
| (198) | N-Isobutyryl 3-Nitroisonicotinamide |
| (199) | N-Valeryl 3-Nitroisonicotinamide |
| (200) | N-Isovaleryl 3-Nitroisonicotinamide |
| (201) | N-Pivaroyl 3-Nitroisonicotinamide |
| (202) | N-Hexanoyl 3-Nitroisonicotinamide |
| (203) | N-Heptanoyl 3-Nitroisonicotinamide |
| (204) | N-Octanoyl 3-Nitroisonicotinamide |
| (205) | N-Nonanoyl 3-Nitroisonicotinamide |
| (206) | N-2-Ethylhexanoyl 3-Nitroisonicotinamide |
| (207) | N-Lauroyl 3-Nitroisonicotinamide |
| (208) | N-Palmitoyl 3-Nitroisonicotinamide |
| (209) | N-Stearoyl 3-Nitroisonicotinamide |
| (210) | N-Acryloyl 3-Nitroisonicotinamide |
| (211) | N-Crotonoyl 3-Nitroisonicotinamide |
| (212) | N-3-Butenoyl 3-Nitroisonicotinamide |
| (213) | N-Methacryloyl 3-Nitroisonicotinamide |
| (214) | N-Benzoyl 3-Nitroisonicotinamide |
| (215) | N-(3,5-Dimethylbenzoyl) 3-Nitroisonicotinamide |
| (216) | N-(3,4-Dimethoxybenzoyl) 3-Nitroisonicotinamide |
| (217) | N-(o-Toluoyl) 3-Nitroisonicotinamide |
| (218) | N-(m-Toluoyl) 3-Nitroisonicotinamide |
| (219) | N-(p-Toluoyl) 3-Nitroisonicotinamide |
| (220) | N-(p-Chlorobenzoyl) 3-Nitroisonicotinamide |
| (221) | N-(p-Bromobenzoyl) 3-Nitroisonicotinamide |
| (222) | N-(p-Methoxybenzoyl) 3-Nitroisonicotinamide |
| (223) | N-(2-Furoyl) 3-Nitroisonicotinamide |
| (224) | N-(2-Thenoyl) 3-Nitroisonicotinamide |
| (225) | 4-(4-Methylallophanoyl)-3-nitropyridine |
| (226) | 4-(4-Ethyallophanoyl)-3-nitropyridine |
| (227) | 4-(4-n-Propylallophanoyl)-3-nitropyridine |
| (228) | 4-(4-Isopropylallophanoyl)-3-nitropyridine |
| (229) | 4-(4-n-Butylallophanoyl)-3-nitropyridine |
| (230) | 3-Nitroisonicotinohydroxamic acid |
| (231) | 2-Methyl-3-nitroisonicotinamide |
| (232) | N-Methyl 2-Methyl-3-nitroisonicotinamide |
| (233) | N-Ethyl 2-Methyl-3-nitroisonicotinamide |
| (234) | N,N-Dimethyl 2-Methyl-3-nitroisonicotinamide |
| (235) | N,N-Diethyl 2-Methyl-3-nitroisonicotinamide |
| (236) | N-Allyl-2-nitro-3-pyridinecarboxide |
| (237) | 3-Nitro-2-pyridinecarboxamide |
| (238) | N-Methyl 3-Nitro-2-pyridinecarboxamide |
| (239) | N-Ethyl 3-Nitro-2-pyridinecarboxamide |
| (240) | N-Propyl 3-Nitro-2-pyridinecarboxamide |
| (241) | N,N-Dimethyl 3-Nitro-2-pyridinecarboxamide |
| (242) | N,N-Diethyl 3-Nitro-2-pyridinecarboxamide |
| (243) | N-Ethyl-N-methyl 3-Nitro-2-pyridinecarboxamide |
| (244) | N-Acetyl 3-Nitro-2-pyridinecarboxamide |
| (245) | N-Propionyl 3-Nitro-2-pyridinecarboxamide |
| (246) | N-Butyryl 3-Nitro-2-pyridinecarboxamide |
| (247) | N-Isobutyryl 3-Nitro-2-pyridinecarboxamide |
| (248) | N-Valeryl 3-Nitro-2-pyridinecarboxamide |
| (249) | N-Isovaleryl 3-Nitro-2-pyridinecarboxamide |
| (250) | N-Pivaroyl 3-Nitro-2-pyridinecarboxamide |
| (251) | N-Hexanoyl 3-Nitro-2-pyridinecarboxamide |
| (252) | N-Heptanoyl 3-Nitro-2-pyridinecarboxamide |
| (253) | N-Octanoyl 3-Nitro-2-pyridinecarboxamide |
| (254) | N-Crotonoyl 3-Nitro-2-pyridinecarboxamide |
| (255) | N-Benzoyl 3-Nitro-2-pyridinecarboxamide |
| (256) | N-(o-Toluoyl) 3-Nitro-2-pyridinecarboxamide |
| (257) | N-(m-Toluoyl) 3-Nitro-2-pyridinecarboxamide |
| (258) | N-(p-Toluoyl) 3-Nitro-2-pyridinecarboxamide |
| (259) | N-(p-Chlorobenzoyl) 3-Nitro-2-pyridinecarboxamide |
| (260) | N-(p-Methoxybenzoyl) 3-Nitro-2-pyridinecarboxamide |
| (261) | N-(2-Thenoyl) 3-Nitro-2-pyridinecarboxamide |
| (262) | 2-(4-Methylallophanoyl)-3-nitropyridine |
| (263) | 2-(4-Ethylallophanoyl)-3-nitropyridine |
| (264) | 3-Nitro-2-pyridinecarbohydroxamic acid |
| (265) | 4-Methyl-3-nitro-2-pyridinecarboxamide |
| (266) | 6-Methyl-3-nitro-2-pyridinecarboxamide |
| (267) | 5-Methyl-3-nitro-2-pyridinecarboxamide |
| (268) | N-Methyl 5-Methyl-3-nitro-2-pyridinecarboxamide |
| (269) | N-Ethyl 5-Methyl-3-nitro-2-pyridinecarboxamide |
| (270) | N,N-Dimethyl 5-Methyl-3-nitro-2-pyridinecarboxamide |
| (271) | N,N-Diethyl 5-Methyl-3-nitro-2-pyridinecarboxamide |
| (272) | N-Acetyl 5-Methyl-3-nitro-2-pyridinecarboxamide |
| (273) | N-Propionyl 5-Methyl-3-nitro-2-pyridinecarboxamide |
| (274) | N-Butyryl 5-Methyl-3-nitro-2-pyridinecarboxamide |
| (275) | 5-Nitro-2-pyridinecarboxamide |
| (276) | N-Methyl 5-Nitro-2-pyridinecarboxamide |
| (277) | N-Ethyl 5-Nitro-2-pyridinecarboxamide |
| (278) | N-Propyl 5-Nitro-2-pyridinecarboxamide |
| (279) | N,N-Dimethyl 5-Nitro-2-pyridinecarboxamide |
| (280) | N,N-Diethyl 5-Nitro-2-pyridinecarboxamide |
| (281) | N-Ethyl-N-methyl 5-Nitro-2-pyridinecarboxamide |
| (282) | N-Hydroxymethyl 5-Nitro-2-pyridinecarboxamide |
| (283) | N-Acetyl 5-Nitro-2-pyridinecarboxamide |
| (284) | N-Propionyl 5-Nitro-2-pyridinecarboxamide |
| (285) | N-Butyryl 5-Nitro-2-pyridinecarboxamide |
| (286) | N-Isobutyryl 5-Nitro-2-pyridinecarboxamide |
| (287) | N-Valeryl 5-Nitro-2-pyridinecarboxamide |
| (288) | N-Isovaleryl 5-Nitro-2-pyridinecarboxamide |
| (289) | N-Hexanoyl 5-Nitro-2-pyridinecarboxamide |
| (290) | N-Heptanoyl 5-Nitro-2-pyridinecarboxamide |
| (291) | N-Octanoyl 5-Nitro-2-pyridinecarboxamide |
| (292) | N-Nonanoyl 5-Nitro-2-pyridinecarboxamide |
| (293) | N-Lauroyl 5-Nitro-2-pyridinecarboxamide |
| (294) | N-Crotonoyl 5-Nitro-2-pyridinecarboxamide |
| (295) | N-Butenoyl 5-Nitro-2-pyridinecarboxamide |
| (296) | N-Benzoyl 5-Nitro-2-pyridinecarboxamide |
| (297) | N-(o-Toluoyl) 5-Nitro-2-pyridinecarboxamide |
| (298) | N-(m-Toluoyl) 5-Nitro-2-pyridinecarboxamide |
| (299) | N-(p-Toluoyl) 5-Nitro-2-pyridinecarboxamide |
| (300) | N-(p-Methoxybenzoyl) 5-Nitro-2-pyridinecarboxamide |
| (301) | N-(p-Chlorobenzoyl) 5-Nitro-2-pyridinecarboxamide |
| (302) | N-(2-Thenoyl) 5-Nitro-2-pyridinecarboxamide |
| (303) | N-(2-Furoyl) 5-Nitro-2-pyridinecarboxamide |
| (304) | 2-(4-Methylallophanoyl)-5-nitropyridine |
| (305) | 2-(4-Ethylallophanoyl)-5-nitropyridine |
| (306) | 5-Nitro-2-pyridinecarbohydroxamic acid |
| (307) | 4-Methyl-5-nitro-2-pyridinecarboxamide |
| (308) | N-Methyl 4-Methyl-5-nitro-2-pyridinecarboxamide |
| (309) | N-Ethyl 4-Methyl-5-nitro-2-pyridinecarboxamide |
| (310) | N,N-Dimethyl 4-Methyl-5-nitro-2-pyridinecarboxamide |
| (311) | N-Acetyl 4-Methyl-5-nitro-2-pyridinecarboxamide |
| (312) | 6-Methyl-5-nitro-2-pyridinecarboxamide |
| (313) | N-Chloroacetyl 2-Methyl-5-nitronicotinamide |

Of the above-listed compounds, there are mentioned the following compounds as a preferable group in view of their anticoccidial activities.

Compounds Nos. 1, 2, 3, 16, 17, 20, 28, 29, 30, 31, 32, 33, 35, 36, 38, 40, 47, 48, 53, 56, 57, 58, 65, 74, 80, 82, 83, 84, 97, 98, 101, 109, 110, 111, 112, 113, 114, 116, 117, 119, 121, 129, 130, 137, 139, 140, 141, 146, 159, 186, 187, 189, 190, 194, 195, 197, 198, 199, 200, 201, 202, 204, 211, 214, 217, 218, 219, 241, 242.

The most preferable group of the above-listed compounds are as follows:

Compounds Nos. 1, 2, 3, 16, 20, 28, 32, 38, 48, 53, 58, 65, 74, 80, 82, 84, 98, 101, 109, 110, 112, 116, 119, 130, 137, 159, 186, 189, 194, 211, 214, 241.

The above-mentioned Compounds Nos. are frequently referred to hereinbelow.
The pyridine compounds of the formula (I) which may be employed in the present invention may be prepared, for instance, by any of the processes as illustratively shown hereunder.
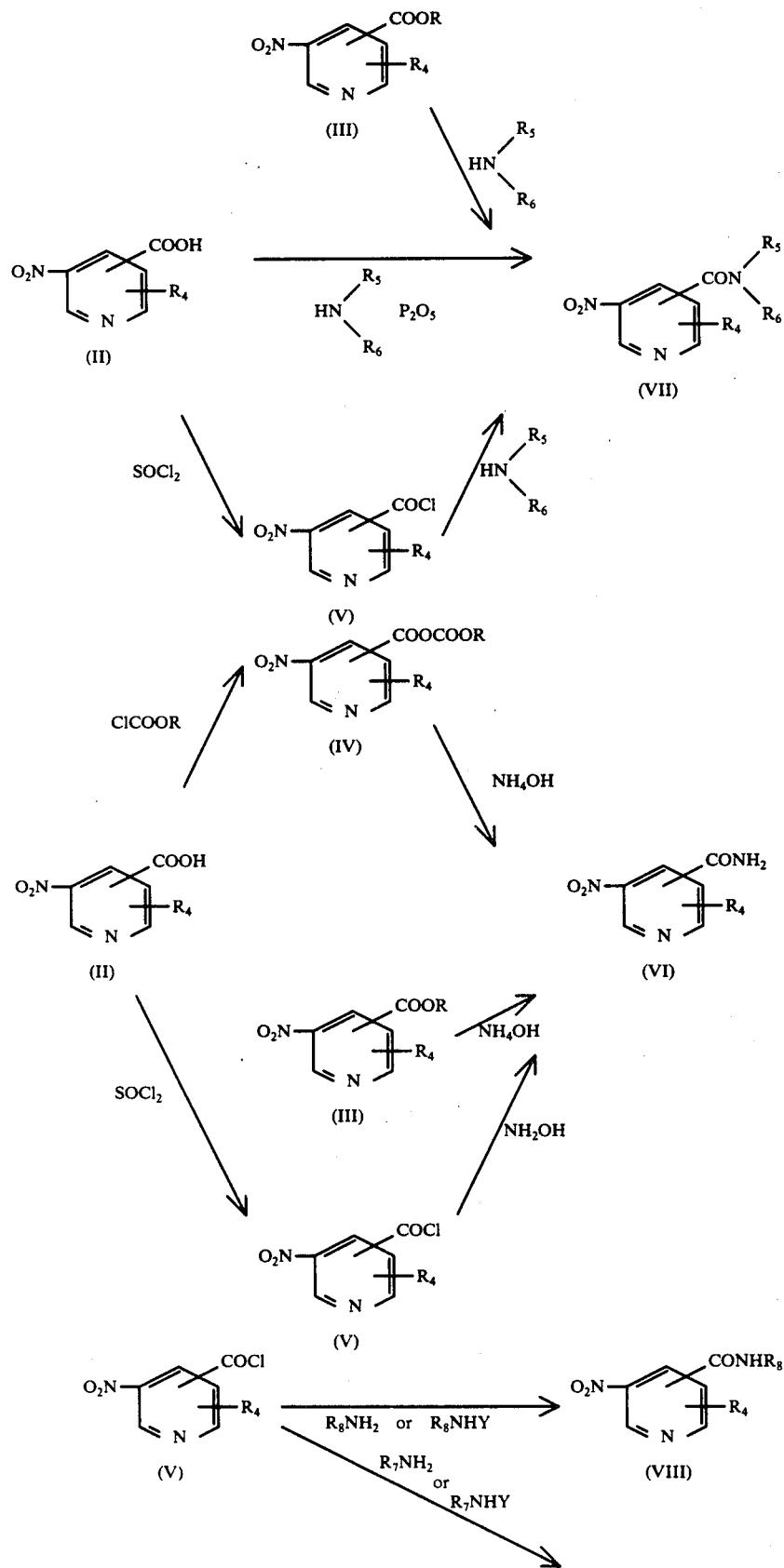

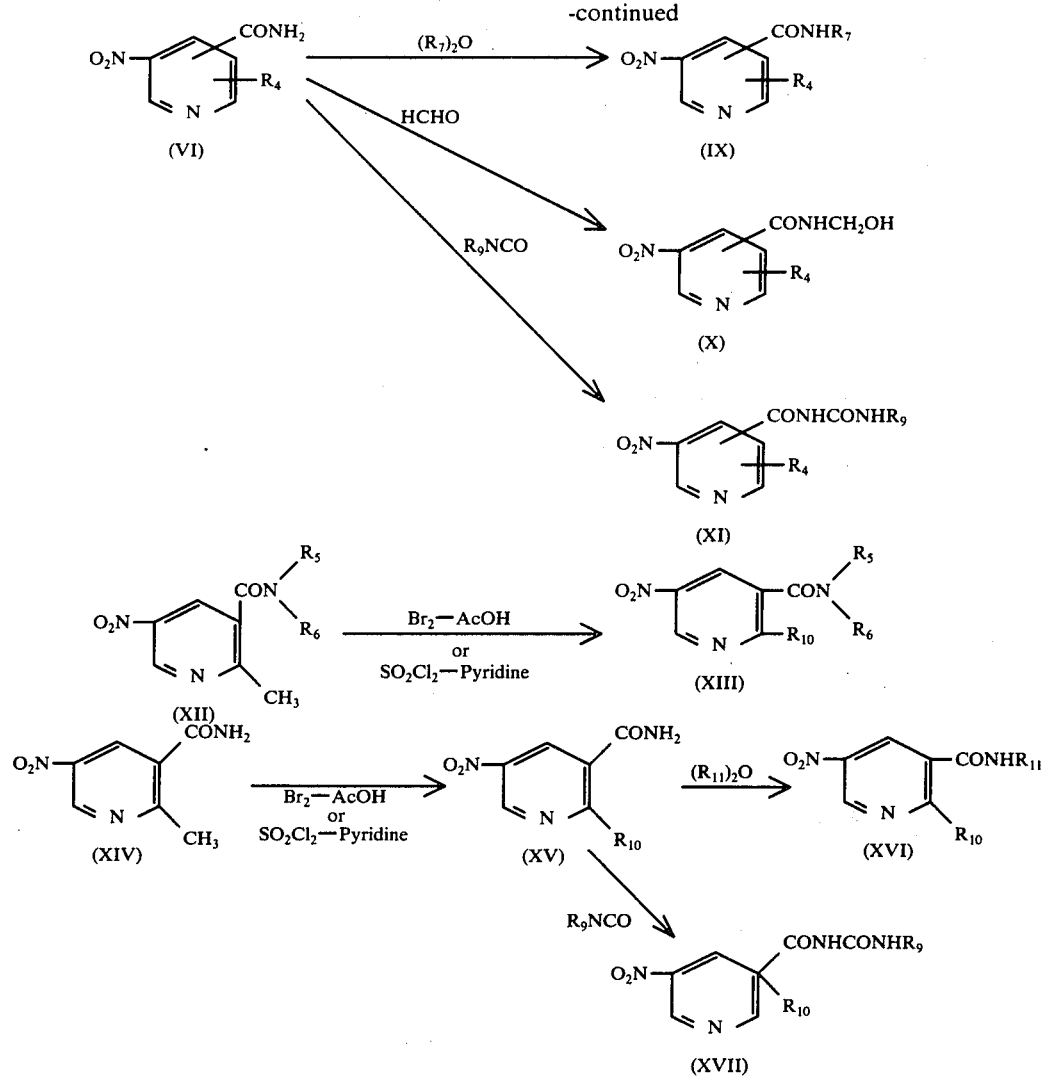

In the above formulae, R is a lower alkyl group; $R_4$ is hydrogen atom or methyl group; $R_5$ and $R_6$ may be the same or different and each represents a lower alkyl group or $R_5$ is hydrogen atom and $R_6$ is a lower alkyl group a lower alkenyl group or a lower alkyl group substituted with OR or hydroxy; $R_7$ is an alkanoyl group, haloacetyl group or an alkenoyl group; $R_8$ is an aromatic acyl group or a heterocyclic acyl group; $R_9$ is a lower alkyl group; $R_{10}$ is halomethyl group; $R_{11}$ is an alkanoyl group or an alkenoyl group; and Y is sodium or potassium atom.

More illustratively, referential examples of the above-listed steps are given below.

1. (III) → (VII)

The compounds (VII) may be prepared from the compound (III) (J. Am. Chem. Soc., 75, 737 (1953)) and the amine.

REFERENTIAL EXAMPLE 1

Synthesis of N-n-butyl 2-methyl-5-nitronicotinamide (No. 87)

To n-butylamine (5 ml.) was added ethyl 2-methyl-5-nitronicotinate (1 g.) and the resulting mixture was stirred at room temperature for 18 hours. The reaction mixture was purified by a silica gel dry column chromatography to give 0.9 g. of the desired pale orange crystals. mp 98° - 99° C.

REFERENTIAL EXAMPLE 2

Synthesis of N-(2-hydroxyethyl) 2-methyl-5-nitronicotinamide (No. 91)

A mixture of ethyl 2-methyl-5-nitronicotinate (1 g.) and 2-aminoethanol (4 ml.) in ethanol (5ml.) was stirred at room temperature for 16 hours. The solvent was distilled off, the residue was purified by silica gel chromatography and recrystallized from ethyl acetate n-hexane to give the desired yellow crystals. mp 144° - 145° C.

In accordance with the above-mentioned process, there were synthesized the following compounds.

N-methyl 2-methyl-5-nitronicotinamide (No. 83) mp 159° - 160° C.

N-ethyl 2-methyl-5-nitronicotinamide (No. 84) mp 152° - 153° C.

N-allyl 2-methyl-5-nitronicotinamide (No. 96) mp 120° - 122° C.

N-isobutyl 2-methyl-5-nitronicotinamide (No. 88) mp 167° - 169° C.

N-(3-methoxypropyl) 2-methyl-5-nitronicotinamide (No. 95) mp 66° – 66.5° C.

2. (II) → (VII)

The compounds (VII) may also be prepared from the compounds (II) by contacting with the amine in the presence of $P_2O_5$, usually at 30° – 100° C., if necessary, in the presence of a suitable organic solvent.

REFERENTIAL EXAMPLE 3

Synthesis of N,N-diethyl 2-methyl-5-nitronicotinamide (No. 98)

In dry chloroform were dissolved 0.3 g of 2-methyl-5-nitronicotinic acid and 1.5 ml of diethylamine. After addition of 10 g of phosphorous pentaoxide, the mixture was stirred with heating at 55° – 60° C for 3 hours. After cooling, the chloroform portion was separated and evaporated under reduced pressure. The residue was, after addition of water, neutralized with sodium hydrogen carbonate and extracted with ethyl acetate. The extract was concentrated and purified on a silica gel column to give 0.25 g of a colorless oil.

Analysis for $C_{11}H_{15}N_3O_3$:
Calcd. (%) : C, 55.68; H, 6.37; N, 17.71.
Found (%) : C, 55.67; H, 6.53; N, 17.60.

Following the above-mentioned process, there were synthesized the compounds below.

N-(2-ethoxyethyl)-N-ethyl 2-methyl-5-nitronicotinamide (No. 106) mp 78° – 80° C.
N-ethyl-N-methyl 2-methyl-5-nitronicotinamide (No. 101) mp 61° – 62° C.
N-allyl 5-nitronicotinamide (No. 15) mp 104° – 105° C.
N-ethoxyethyl 5-nitronicotinamide (No. 13)

3. (II) → (V) → (VII)

The compounds (VII) may be prepared by reacting the compounds (II) [Chem. Pharm. Bull., 13, 113 (1965)] with thionyl chloride to give an acid chloride and then bringing the acid chloride into contact with the amine.

REFERENTIAL EXAMPLE 4

Synthesis of N,N-dimethyl 5-nitronicotinamide (No. 16)

0.8 g of 5-nitronicontinic acid and 40 g of thionyl chloride were refluxed for 4 hours, and an excess of the thionyl chloride was distilled off. The residue was then dissolved in 10 ml of anhydrous ether and the solution was slowly added to 7 ml of 20% aqueous dimethylamine solution to precipitate crystals. The obtained crystals were recrystallized from water to give 0.27 g of the desired compound. mp 109° – 110° C.

N-ethyl-N-methyl 5-nitronicotinamide (No. 20) mp 65° C.
N-ethoxyethyl-N-ethyl 5-nitronicotinamide (No. 25) Colorless oil Analysis for $C_{12}H_{17}N_3O_4$:
Calcd. (%) : C, 53.92; H, 6.41; N, 15.72.
Found (%) : C, 53.69; H, 6.47; N, 15.57.

N-methyl 5-nitronicotinamide (No. 2) mp 180° – 181° C.
N-ethyl 5-nitronicotinamide (No. 3) mp 167° C.
N-n-butyl 5-nitronicotinamide (No. 6) mp 101° – 102° C.
N-(2-hydroxyethyl) 5-nitronicotinamide (No. 10) mp 108° – 109° C.
5-nitronicotinohydroxamic acid (No. 80) mp 184° – 185° C. (with decomp.)
2-methyl-5-nitronicotinohydroxamic acid (No. 159) mp 164° – 166° C. (with decomp.)
N-methyl 3-nitroisonicotinamide (No. 186) mp 157° – 158° C.
N,N-dimethyl 3-nitroisonicotinamide (No. 189)
N-allyl 3-nitroisonicotinamide (No. 192) mp 91° – 92° C.
N,N-diethyl 2-methyl-3-nitroisonicotinamide (No. 235) oil Analysis for $C_{11}H_{15}N_3O_3$:
Calcd. (%) : C, 55.68; H, 6.37; N, 17.71.
Found (%) : C, 55.49; H, 6.54; N, 17.66.

N-ethyl 3-nitro-2-pyridinecarboxamide (No. 239) mp 88° – 89° C.
N-allyl 3-nitro-2-pyridinecarboxamide (No. 236) mp 87° – 88° C.
N,N-dimethyl 3-nitro-2-pyridinecarboxamide (No. 241) oil Analysis for $C_8H_9N_3O_3$:
Calcd. (%) : C, 49.23; N, 4.65; N, 21.53.
Found (%) : C, 49.37; H, 4.72; N, 21.71.

N-methyl 5-methyl-3-nitro-2-pyridinecarboxamide (No. 268) mp 152° – 153° C.
N-methyl 5-nitro-2-pyridinecarboxamide (No. 276) mp 158° – 160° C.
N,N-dimethyl 5-nitro-2-pyridinecarboxamide (No. 279) mp 116° – 117° C.

4. (II) → (IV) → (VI)

The compounds (VI) may be prepared from the compounds (II) by reacting with the chloroformate and then contacting with ammonia.

5-nitro-2-pyridinecarboxamide (No. 275) mp 246° C.
6-methyl-5-nitro-2-pyridinecarboxamide (No. 312) mp 170° – 171° C.

5. (III) → (VI)

The compounds (VI) may also be prepared from the compounds (III) according to the method disclosed in Chem. Pharm. Bull., 13, 113 (1965).

5-nitronicotinamide as disclosed in the above.

6. (II) → (V) → (VI)

The compounds (VI) may also be prepared from the compounds (II) by reacting with thionyl chloride and then contacting with ammonia.

REFERENTIAL EXAMPLE 5

Synthesis of 2-methyl-3-nitroisonicotinamide (No. 231)

A mixture of 0.5 g 2-methyl-3-nitroisonicotinic acid and 20 ml of thionyl chloride was refluxed gently for 30 min. and the excess thionyl chloride was removed in vacuo to leave an oil, which was treated with conc. $NH_4OH$ under cooling for 20 min. and extracted with EtOAc. The extract was washed with water and dried, the solvent was removed to give an oil, which was purified over silica gel to yield 0.2 g of 2-methyl-3-nitroisonicotinamide, mp 203° – 204° C.

Following the above process, there were synthesized the following compounds.

6-methyl-3-nitro-2-pyridinecarboxamide (No. 266) mp 160° – 162° C.
4-methyl-3-nitro-2-pyridinecarboxamide (No. 265) mp 243° – 244° C.
4-methyl-5-nitro-2-pryidinecarboxamide (No. 307) mp 180° – 182° C.

7. (V) → (VIII)

The compounds (VIII) may be prepared from the compounds (V) by contacting sodium or potassium salt of the acid amide in the presence of a suitable solvent at room temperature.

REFERENTIAL EXAMPLE 6

Synthesis of N-(2-thenoyl) 5-nitronicotinamide (No. 71)

A mixture of 2 g of 5-nitronicotinic acid and 30 ml. of thionyl chloride was refluxed for 3 hours. Excess thionyl chloride was distilled off to give oily 5-nitronicotinoyl chloride. The acid chloride thus obtained was added to 10 ml of pyridine at −15° C. and 1.4 g of 2-thiophene carboxamide was added thereto. The resulting mixture was stirred at room temperature for 16 hours. The solvent was distilled off under reduced pressure at a temperature below 40° C. and the residue was purified over silica gel chromatography and recrystallized from ethyl acetate-n-hexane to give 200 mg of the desired product. mp 187° C.

Following the above process, there were synthesized the following compounds.

N-benzoyl 2-methyl-5-nitronicotinamide (No. 137) mp 155° – 157° C.
N-benzoyl 5-nitronicotinamide (No. 53) mp 176° – 177° C.
N-(p-toluoyl) 5-nitronicotinamide (No. 58) mp 172° – 174° C.
N-(p-methoxybenzoyl) 5-nitronicotinamide (No. 65) mp 146° – 147° C.
N-(p-chlorobenzoyl) 5-nitronicotinamide (No. 62) mp 166° – 167° C.
N-nicotinoyl 5-nitronicotinamide (No. 73) mp 164° – 166° C.
N-(5-nitronicotinoyl) 5-nitronicotinamide (No. 74) mp 191° – 193° C.
N-benzoyl 3-nitroisonicotinamide (No. 214) mp 142° – 143° C.

8. (V) → (IX)

The compounds (IX) may be prepared from the compounds (V) by contacting sodium or potassium salt of the acid amide in the presence of a suitable solvent at room temperature.

REFERENTIAL EXAMPLE 7

Synthesis of N-acetyl 5-nitronicotinamide (No. 28)

In 10 ml of dimethylformamide was dissolved 0.29 g of acetamide, and to this solution was added 0.24 g of NaH (mineral oil 50%). The mixture was then stirred at room temperature for 2 hours. To the mixture was added 0.93 g of 5-nitronicotinic acid chloride, and this was stirred overnight at room temperature. The solvent was evaporated under reduced pressure. The obtained residue was, after addition of water, extracted with ethyl acetate. The extract was dried over sodium sulfate and evaporated to remove the solvent. The obtained product was purified on a silica gel column and recrystallized from ethyl acetate - petroleum ether to give 0.07 g of the desired compound melting at 162° – 163° C.

Following the above-mentioned process, there were synthesized the compounds below.

N-Valeryl 5-nitronicotinamide (No. 32) mp 116° – 118° C.
N-Octanoyl 5-nitronicotinamide (No. 38) mp 108° – 109° C.
N-Crotonoyl 5-nitronicotinamide (No. 48) mp 175° – 177° C.

9. (VI) → (IX)

The compounds (IX) may be prepared from the compounds (VI) by contacting with the acid anhydride at 10° – 150° C.

REFERENTIAL EXAMPLE 8

Synthesis of N-propionyl 2-methyl-5-nitronicotinamide (No. 110)

To 0.5 g of 2-methyl-5-nitronicotinamide were added 3 ml of propionic anhydride and five drops of conc. sulfuric acid, and the mixture was stirred at room temperature for 16 hours. After completion of the reaction, water was added to the reaction mixture, and the resulting mixture was stirred at room temperature for one hour, made alkaline with 5% aqueous sodium hydrogen carbonate solution and extracted with ethyl acetate. The extract was then purified on a silica gel column to give 0.36 g of the desired compound as white crystals. mp 171° – 173° C.

REFERENTIAL EXAMPLE 9

Synthesis of N-pivaloyl 2-methyl-5-nitronicotinamide (No. 116)

A mixture of 1.0 g of 2-methyl-5-nitronicotinamide, 6-ml of pivalic anhydride and five drops of conc. sulfuric acid was stirred with heating at 90° C for 90 hours. After completion of the reaction, the mixture was treated in the same manner as above to give 0.31 g of the desired compound. mp 138° – 139° C.

Following the above-mentioned process, there were synthesized the compounds below.

N-Acetyl 2-methyl-5-nitronicotinamide (No. 109) mp 200° – 201° C.
N-Crotonoyl 2-methyl-5-nitronicotinamide (No. 130) mp 146° – 148° C.
N-Isobutyryl 2-methyl-5-nitronicotinamide (No. 112) mp 185° – 187° C.
N-Valeryl 2-methyl-5-nitronicotinamide (No. 113) mp 162° – 163° C.
N-Octanoyl 2-methyl-5-nitronicotinamide (No. 119) mp 125° – 126° C.
N-Palmitoyl 2-methyl-5-nitronicotinamide (No. 127) mp 105° – 108° C.
N-Stearoyl 2-methyl-5-nitronicotinamide (No. 128) mp 108° – 110° C.
N-Acetyl 5-nitronicotinamide (No. 28) mp 162° – 163° C.

N-Chloroacetyl 2-methyl-5nitronicotinamide (No. 313) mp 155° – 156° C.

N-Acetyl 3-nitroisonicotinamide (No. 194) mp 175° – 176° C.

N-Crotonoyl 3-nitroisonicotinamide (No. 211) mp 150° – 152° C.

N-Crotonoyl 3-nitro-2-pyridinecarboxamide (No. 254) mp 161° – 163° C.

N-Octanoyl 3-nitro-2-pyridinecarboxamide (No. 253) mp 63° – 64° C.

N-Acetyl 5-nitro-2-pyridinecarboxamide (No. 283) mp 150° – 152° C.

N-Propionyl 5-nitro-2-pyridinecarboxamide (No. 284) mp 94° – 96° C.

N-Octanoyl 5-nitro-2-pyridinecarboxamide (No. 291) mp 73° – 74° C.

10. (VI) →(X)

The compounds (X) may be prepared from the compounds (VI) by heating with formalin at 50° – 100° C.

REFERENTIAL EXAMPLE 10

Synthesis of N-hydroxymethyl 5-nitronicotinamide (No. 9)

A solution of 1.0 g of 5-nitronicotinamide and 2ml of 37% formalin in 3 ml of dimethylformamide was stirred at 100° C. for 2 hours. After cooling, ice-water was added and the mixture was extracted with ethyl acetate. The extract was chromatographed over silica gel and recrystallized from ethanol to give 0.6 g of the desired product. mp 145° – 146° C.

11. (VI) →(XI)

The compounds (XI) may be prepared from the compounds (VI) by heating with the isocyanate at 100° – 180° C. in the presence or absence of a suitable solvent.

REFERENTIAL EXAMPLE 11

Synthesis of 3-(4-n-butylallophanoyl)-2-methyl-5-nitropyridine (No. 157)

A mixture of 0.9 g of 2-methyl-5-nitronicotinamide and 0.9 g of n-butylisocyanate in 40 ml of anhydrous toluene was refluxed for 18 hours. Unreacted nicotinamide (0.2 g) was filtered off and the filtrate was chromatographed over silica gel to give 0.6 g of the desired product. mp 111° – 112° C.

Following the above process, there were synthesized the following compounds.

3-(4-Ethylallophanoyl)-2-methyl-5-nitropyridine (No. 154) mp 164° – 166° C.

3-(4-Isopropylallophanoyl)-2-methyl-5-nitropyridine (No. 156) mp 154° – 156° C.

3-(4-Ethylallophanoyl)-5-nitropyridine (No. 76) mp 215° – 216° C.

4-(4-Ethylallophanoyl)-3-nitropyridine (No. 226) mp 129° – 130° C.

12. (XII) → (XIII), (XIV) → (XV) → (XVI) and
(XIV) → (XV) → (XVII)

These steps may be conducted as shown above according to conventional methods.

REFERENTIAL EXAMPLE 12

[(XII) → (XIII)]

Synthesis of N,N-diethyl 2-bromomethyl-5-nitronicotinamide

To a solution of 0.6 g of 2-methyl-5-nitronicotinic acid and 3 ml of diethylamine in 100 ml of chloroform was added 20 g of phosphorus pentachloride and the resulting mixture was stirred at 60° C. for 3 hours. After cooling, the chloroform layer was separated, the solvent was distilled off under reduced pressure, the residue was mixed with water, neutralized with sodium bicarbonate and extracted with ethyl acetate. The extract was dried, concentrated and chromatographed over silica gel to give 0.4 g of the desired product as oil.

Analysis for $C_{11}H_{15}N_3O_3$ : Calcd. (%): C, 55.68; H, 6.37; N, 17.71. Found (%) : C, 55.57; H, 6.43; N, 17.56.

To a solution of 0.4 g of N,N-diethyl-2-methyl-5-nitronicotinamide in 1.5 ml of acetic acid was added a solution of 0.27 g of bromine in 1.0 ml of acetic acid and the resulting mixture was stirred at 120° C. for 1.5 hours. The reaction mixture was poured into ice-water, made alkaline with sodium bicarbonate and extracted with ethyl acetate. The extract was washed with water, dried and the solvent was distilled off to give brown oily substance. This substance was chromatographed over silica gel to give 0.1 g of unreacted starting material and 0.28 g of N,N-diethyl 2-bromomethyl-5-nitronicotinamide. mp 62° – 64° C.

REFERENTIAL EXAMPLE 13

[(XIV) → (XV)]

Synthesis of 2-dibromomethyl-5-nitronicotinamide (No. 161)

To a solution of 1.0 g of 2-methyl-5-nitronicotinamide in 10 ml of acetic acid was added dropwise a solution of 8 g of bromine in 15 ml of acetic acid and the mixture was stirred at 130° C. for 1 hour. After completion of the reaction, the solvent was distilled off, made alkaline with aqueous sodium bicarbonate and extracted with ethyl acetate. The extract was washed with water, dried and the solvent was distilled off to give brown oily substance. This substance was chromatographed over silica gel to give 1.2 g of the desired product as yellow needles. mp 156° – 158° C. (with decomp.)

REFERENTIAL EXAMPLE 14

[(XIV) → (XV)]

Synthesis of 2-dichloromethyl-5-nitronicotinamide (No. 163)

A solution of 0.5 g of 2-methyl-5-nitronicotinamide and 5 ml of sulfuryl chloride in 1 ml of pyridine was stirred at room temperature for 48 hours. The reaction mixture was poured into ice-water, made alkaline with sodium bicarbonate and extracted with ethyl acetate. The extract was washed with water, dried and the solvent was distilled off to give brown oily substance. This substance was chromatographed over silica gel to give 0.23 g of the desired product as yellow needles. mp 125° – 127° C.

Following the above process, there were synthesized the following compounds.

N,N-diethyl 2-dibromomethyl-5-nitronicotinamide (No. 170) mp 79° – 80° C.

2-bromomethyl-5-nitronicotinamide (No. 160) mp 160° – 162° C.

REFERENTIAL EXAMPLE 15

[(XV) → (XVI)]

Synthesis of N-acetyl 2-dibromomethyl-5-nitronicotinamide (No. 173)

A mixture of 0.48 g of 2-dibromomethyl-5-nitronicotinamide and acetic anhydride was stirred with 3 drops of conc. sulfuric acid at room temperature for 1 hour. The reaction mixture was poured into ice-water, made alkaline with 5% sodium bicarbonate and extracted with ethyl acetate. The extract was dried and the solvent was distilled off to give 0.35 g of crystalline substance, which was then recrystallized from ethyl acetate-n-hexane to give the desired product as yellow needles. mp 168° C. (with decomp.)

The compounds of the formula (I) or the salts thereof are conveniently fed to poultry as a component of the feed or drinking water, but they may also be administered orally dispersed or admixed with other carriers.

According to one aspect of this invention, novel compositions are provided in which a pyridine derivative or the salt thereof (I) is present as an active ingredient. Such compositions comprise the pyridine derivative intimately dispersed in or admixed with an inert carrier. The term "inert carrier" as used herein means one that is substantially non-reactive with the active ingredient, orally ingestable and tolerated by the poultry.

The amount of pyridine derivative required for control of coccidiosis in poultry will vary somewhat with the specific compound employed, the species of animals, the method or the object of application or with the symptoms. Generally, the pyridine derivatives (I) are effective in preventing the disease without undesirable side effect and toxic effect when administered at a level of more than about 0.004% by weight of the feed. For good prophylactic results, it is preferred that the feed contains between about 0.004 and 0.025% by weight of the active ingredient, more preferably between about 0.0075 and 0.0125%. When the pyridine derivatives are to be employed for therapeutic purpose, the higher levels are used for a shorter period of time. Thus, the concentrations of about 0.05% to about 0.1% by weight of the feed may be advantageously administered for treatment of coccidiosis. When these compounds are to be employed for therapeutic purposes, it is desirable to employ the lowest levels that exhibit anticoccidial activities, in order to eliminate any risk of side effects that may appear on prolonged feeding.

In preparing solid compositions, a uniform dispersion of the active ingredient throughout the carrier can be readily accomplished by the conventional methods of grinding, stirring or milling.

Many of these pyridine derivatives or the salts thereof are advantageously administered to poultry by way of the drinking water of the birds. This method of treatment may often be employed in the therapeutic use, since poultry with coccidiosis are apt to consume less solid feed than normal birds.

According to another aspect of this invention, novel compositions are provided in which active ingredient is present in relatively large amounts and which are suitable for addition to the poultry feed directly or after intermediate dilution step. Such compositions which are a preferred feature of this invention are the so-called feed supplements or premix. Representative examples of the carriers to be employed in this invention are solid oral carriers such as distillers dried grains, corn starch, potato starch, fermentation residues, ground oyster shells, Attapulgus clay, rice bran, wheat bran, wheat middling, molasses solubles, corn meal, edible vegetable substances, soybean cake, soybean meal, antibiotic mycelis, crushed lime stone and the like. The salts are intimately dispersed or admixed throughout the solid inert carrier as described hereinabove. Formulations containing from about 5% to about 30% by weight, and preferably from about 10 – 25% by weight, of the active ingredient are particularly suitable for this purpose. It is preferable in the industry to use about 1 – 3 kg of such a supplement per ton of feed.

According to another aspect of this invention, the present composition may preferably include other known anticoccidial agents to broaden its anticoccidial spectrum and, sometimes, expect a synergistic effect. Suitable examples of such anticoccidial agents include, for example, sulfa drugs, e.g., Sulfachloropyrazine, Sulfadimethoxine, Sulfaquinoxaline; thiamine derivatives, e.g., Beclotiamine, Amprolium, Dimethialium; quinoline derivatives, e.g., Buquinolate, Decoquinate, Methyl Benzoquate; folic acid antagonistic substances, e.g., pyrimethamin, Diaveridine; antibiotics, e.g., Monensin; Zolene (3,5-dinitro-o-toluamide), Clopidol (3,5-dichloro-2,6-dimethyl-4-pyridinol), Robenzidine; and the like.

The formulation of the compounds and the coccidiostatic activity of the compounds are more fully illustrated by the non-limiting examples as follows.

In these examples, all the parts are given by weight unless otherwise indicated.

The following are three typical formulations for feed supplements in accordance with the present invention:

| Formulation A | parts by weight |
|---|---|
| 5-nitronicotinamide | 25 |
| wheat bran | 75 |
| Formulation B | parts by weight |
| N-methyl 5-nitronicotinamide | 20 |
| rice bran | 80 |
| Formulation C | parts by weight |
| 2-methyl 5-nitronicotinamide | 10 |
| soybean meal | 90 |

The coccidiostatic activity of the pyridine derivatives (I) or the salts thereof of this invention is determined by the following method:

TEST PROCEDURES

1. Chicks: Fourteen-day-old White Leghorn males (after being hatched, fed a diet containing no anticoccidial agent and isolated as far as possible from the risk of extraneous coccidial infections) were used.

Each group consisted of 10 chicks so as to avoid the difference of mean weight (significance level, 5%).

2. Infections: Each chick was inoculated orally into the crop with 42,000 sporulated oocysts of *Eimeria tenella*.

3. Concentration of tested compounds: Each tested compound as indicated below was mixed to the commercially available mixed feed at the concentration of 200 ppm.

4. Test procedures: The above chicks were isolated from those suffering coccidiosis and observed on their states of health. Normal healthy chicks were weighed and divided into groups, each consisting of 10 chicks so as to avoid the significant difference of average body weight (significance level 5%). On the other hand, two control groups of infected and non-medicated chicks and non-infected and non-medicated ones were separately prepared. After dividing into groups, a given number of occysts was inoculated to all groups except for the non-infected and non-medicated control group, simultaneously with the feeding of a diet containing the test compound. Two control groups were fed with a diet which has the same formula (the same lot) and no test compound. (5) Evaluation: They are weighed from the beginning of the test to the end (when administered and infected) constantly. Daily oocyst outputs are determined as oocysts per gram feces during a period from day 4 to 6 after infection. The daily samples from each treatment are pooled and recorded as a percentage to that of the infected and non-medicated control. After 7 days from the infection, all chicks are sacrificed and the degree of the lesion of ceca are indicated as a 0 to 4 visual scale and determined by the method of Johnson and Reid described in Experimental Parasitology vol. 28, 30 – 36 pp., (1970).

Evaluation item's values are calculated according to the following equations, respectively.

(i)
$$\text{Rate of oocyst production (\%)} = \frac{\text{Oocyst outputs of each group}}{\text{Oocyst outputs of infected and non-medicated group}} \times 100$$

The accumulated oocyst outputs per gram feces, on 6 or 7 days after infection, is defined as "oocyst number".

(ii)
$$\text{Relative rate of weight gain (\%)} = \frac{\text{Average weight gain of each group}}{\text{Average weight gain of non-infected and non-medicated group}} \times 100$$

The total of the weight gain from the beginning of the test to the end divided with the number of the chicks is defined as "average weight gain".

(iii)
$$\text{Mean lesion score of cecum} = \frac{\text{Total cecum lesion of scores}}{\text{Number of chicks}}$$

(iv)
$$\text{Mortality} = \frac{\text{Number of chicks at the end of test}}{\text{Number of chicks at the beginning of test}} \times 100$$

The results are listed in the following Table.

Table

| Compound No. | Rate of oocyst production (%) | Relative rate of weight gain (%) | Mean lesion score of cecum | Mortality (%) |
| --- | --- | --- | --- | --- |
| 1 | 0 | 98.0 | 0 | 0 |
| 2 | 0 | 98.5 | 0 | 0 |
| 3 | 0 | 98.5 | 0 | 0 |
| 6 | 4.9 | 89.0 | 1.2 | 0 |
| 9 | 0 | 98.0 | 0 | 0 |
| 10 | 0 | 97.5 | 0.1 | 0 |
| 13 | 14.0 | 85.0 | 2.0 | 0 |
| 15 | 0.5 | 90.0 | 0.8 | 0 |
| 16 | 0 | 98.5 | 0 | 0 |
| 20 | 0 | 98.0 | 0 | 0 |
| 25 | 14.5 | 80.0 | 2.0 | 0 |
| 28 | 0 | 98.5 | 0 | 0 |
| 32 | 0 | 98.0 | 0 | 0 |
| 38 | 0 | 97.5 | 0 | 0 |
| 48 | 0 | 98.3 | 0 | 0 |
| 80 | 0 | 96.5 | 0 | 0 |
| 159 | 0 | 97.0 | 0 | 0 |
| 82 | 0 | 98.0 | 0 | 0 |
| 84 | 0 | 98.0 | 0 | 0 |
| 87 | 4.8 | 87.0 | 1.0 | 0 |
| 88 | 5.8 | 85.0 | 1.2 | 0 |
| 91 | 1.4 | 93.0 | 0.8 | 0 |
| 95 | 18.5 | 83.0 | 2.4 | 0 |
| 96 | 0 | 95.0 | 0.4 | 0 |
| 98 | 0 | 98.5 | 0 | 0 |
| 106 | 8.9 | 85.0 | 2.2 | 0 |
| 101 | 0 | 98.0 | 0 | 0 |
| 109 | 0 | 98.5 | 0 | 0 |
| 110 | 0 | 98.8 | 0 | 0 |
| 130 | 0 | 98.5 | 0 | 0 |
| 112 | 0 | 98.6 | 0 | 0 |
| 113 | 0 | 98.7 | 0 | 0 |
| 116 | 0 | 98.6 | 0 | 0 |
| 119 | 0 | 98.5 | 0 | 0 |
| 127 | 0 | 98.5 | 0 | 0 |
| 128 | 0 | 98.6 | 0 | 0 |
| 160 | 2.1 | 93.5 | 0.3 | 0 |
| 161 | 0.3 | 94.9 | 0.1 | 0 |
| 170 | 0 | 95.5 | 0 | 0 |
| 163 | 0 | 98.0 | 0 | 0 |
| 154 | 0 | 98.5 | 0 | 0 |
| 156 | 0 | 95.0 | 0.2 | 0 |
| 157 | 5.5 | 82.9 | 1.2 | 0 |
| 76 | 12.5 | 78.7 | 1.5 | 0 |
| 313 | 0 | 92.1 | 0.9 | 0 |
| 53 | 0 | 95.6 | 0 | 0 |
| 137 | 0 | 96.1 | 0 | 0 |
| 58 | 0 | 98.6 | 0 | 0 |
| 65 | 0 | 94.5 | 0 | 0 |
| 62 | 0.6 | 92.7 | 0.5 | 0 |
| 73 | 1.4 | 89.2 | 1.1 | 0 |
| 74 | 0 | 98.6 | 0 | 0 |
| 71 | 0.7 | 92.8 | 0.4 | 0 |
| 275 | 1.0 | 90.0 | 0.9 | 0 |
| 312 | 3.0 | 87.0 | 1.5 | 0 |
| 186 | 0 | 92.0 | 0 | 0 |
| 189 | 0 | 92.7 | 0 | 0 |
| 192 | 0.5 | 90.8 | 0 | 0 |
| 194 | 0 | 93.5 | 0 | 0 |
| 211 | 0.1 | 92.5 | 0 | 0 |
| 214 | 0 | 93.5 | 0 | 0 |
| 226 | 0.2 | 92.5 | 0 | 0 |
| 231 | 1.0 | 90.0 | 0.6 | 0 |
| 239 | 0 | 92.5 | 0.2 | 0 |
| 236 | 0.9 | 90.5 | 0.6 | 0 |
| 241 | 0 | 93.5 | 0 | 0 |
| 254 | 0.4 | 91.2 | 0.5 | 0 |
| 253 | 0.3 | 89.8 | 0.5 | 0 |
| 268 | 8.9 | 85.5 | 1.8 | 0 |
| 266 | 0 | 94.0 | 0 | 0 |
| 276 | 1.3 | 92.0 | 0.6 | 0 |
| 279 | 0.9 | 91.5 | 0.6 | 0 |
| 283 | 0.1 | 94.0 | 0 | 0 |
| 284 | 0.2 | 93.5 | 0 | 0 |
| 291 | 0.2 | 94.0 | 0.1 | 0 |
| 307 | 0.3 | 94.0 | 0 | 0 |
| Infected-non-medicated control | 100 | 50 | 4.0 | 30 |
| Uninfected-non-medicated control | 0 | 100 | 0 | 0 |

It will be evident from the above results that the pyridine derivatives of the abovementioned formula (I) or the salts thereof possess an extremely high degree of activity which cause coccidiosis, accompanying with good weight gain of the poultry without any unfavorable side effects.

What is claimed is:

1. An anticoccidial composition containing a minor amount, sufficient for the treatment of coccidiosis, which comprises a compound having the formula

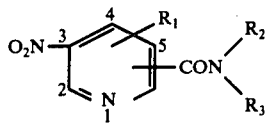 (I)

intimately dispersed in an inert edible carrier, wherein
$R_1$ is hydrogen atom, a halomethyl group or methyl group;
$R_2$ is hydrogen atom or an alkyl group of 1–3 carbon atoms;
$R_3$ is hydrogen atom, an alkyl group of 1–3 carbon atoms, allyl group, an alkyl group having 2 or 3 carbon atoms and alkoxy of 1 or 2 carbon atoms as a substituent, an alkyl group having 1–3 carbon atoms and hydroxy as a substituent, an alkanoyl group of 1–18 carbon atoms, a haloacetyl group, an alkenoyl group of 3–11 carbon atoms, an aromatic acyl group selected from the group consisting of benzoyl, 2,3-dimethoxybenzoyl, 3,4-dimethoxybenzoyl, 3,5-dimethoxybenzoyl, o-, m-, p-toluoyl, o-, m-, p-chlorobenzoyl, o-, m-, p-bromobenzoyl, p-methoxybenzoyl, o-, m-, p-acetylaminobenzoyl, o-, m-, p-cyanobenzoyl, 2-ethoxy-4-acetylaminobenzoyl, 2-ethoxy-4-dimethyl-aminobenzoyl, 2-methoxy-4-acetylaminobenzoyl, 3,5-dimethylbenzoyl, and 3,4-dimethylbenzoyl, a heterocyclic acyl group selected from the group consisting of 2-furoyl, 2-thenoyl, isonicotinoyl, nicotinoyl, 5-nitronicotinoyl and 2-methyl-5-nitronicotinoyl, an N-alkylcarbamoyl group of 1–4 carbon atoms in the alkyl moiety or hydroxy group;
or an inorganic acid addition salt thereof;
provided that when $R_2$ is said alkyl group of 1–3 carbon atoms, $R_3$ is said alkyl group of 1–3 carbon atoms, and provided that the compound of formula (I) is not defined by a methyl group at the 6-position and a —$CONH_2$ group at the 5-position.

2. The anticoccidial composition according to claim 1 wherein
$R_2$ is hydrogen atom or an alkyl group of 1 or 2 carbon atoms;
$R_3$ is hydrogen atom, an alkyl group of 1 or 2 carbon atoms, allyl group, an alkoxyethyl group of 1 or 2 carbon atoms in the alkoxy moiety, a hydroxyalkyl group or 1 or 2 carbon atoms, an alkanoyl group of 1–9 carbon atoms, chloroacetyl group, an alkenoyl group of 3 or 4 carbon atoms, a benzoyl group which may be substituted with methyl, methoxy or halogen, nicotinoyl group, 5-nitronicotinoyl group, 2-thenoyl group, an N-alkylcarbamoyl group of 1 or 2 carbon atoms in the alkyl moiety or hydroxy group;
provided that when $R_2$ is said alkyl group, $R_3$ is said alkyl group of 1 or 2 carbon atoms.

3. The anticoccidial composition according to claim 1 wheren
$R_1$ is attached to the pyridine ring at the 6-position thereof and is hydrogen atom or methyl group, the

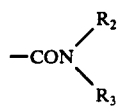

group is attached to the pyridine ring at the 5-position thereof and
$R_2$ is hydrogen atom or an alkyl group of 1 or 2 carbon atoms;
$R_3$ is hydrogen atom, and alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1–9 carbon atoms, an alkenoyl group of 3 or 4 carbon atoms, a benzoyl group which may be substituted with methyl, methoxy or halogen, nicotinoyl group, 2 -thenoyl group, an N-alkylcarbamoyl group of 1 or 2 carbon atoms in the alkyl moiety or hydroxy group;
provided that when $R_2$ is said alkyl group, $R_3$ is said alkyl group of 1 or 2 carbon atoms.

4. The antiococcidial composition according to claim 1 wherein
$R_1$ is attached to the pyridine ring at the 2-position thereof and is hydrogen atom or methyl group, the

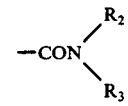

group is attached to the pyridine ring at the 4-position thereof and
$R_2$ is hydrogen atom or an alkyl group of 1 or 2 carbon atoms;
$R_3$ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1–9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;
provided that when $R_2$ is said alkyl group, $R_3$ is said alkyl group of 1 or 2 carbon atoms.

5. The anticoccidial composition according to claim 1 wherein
$R_1$ is hydrogen atom or methyl group, the

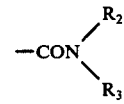

group is attached to the pyridine ring at the 2-position thereof and
$R_2$ is hydrogen atom or an alkyl group of 1 or 2 carbon atoms;
$R_3$ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1–9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;

provided that when R₂ is said alkyl group, R₃ is said alkyl group of 1 or 2 carbon atoms.

6. The anticoccidial composition according to claim 1 wherein

R₁ is attached to the pyridine ring at the 2 or 4-position thereof and is hydrogen atom or methyl group, the

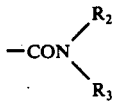

group is attached to the pyridine ring at the 6-position thereof and

R₂ is hydrogen atom or an alkyl group of 1 or 2 carbon atoms;

R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1-9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;

provided that when R₂ is said alkyl group, R₃ is said alkyl group of 1 or 2 carbon atoms.

7. The anticocidial composition according to claim 1 wherein said compound is selected from the group consisting of 5-Nitronicotinamide
N-Methyl 5-Nitronicotinamide
N-Ethyl 5-Nitronicotinamide
N,N-Dimethyl 5-Nitronicotinamide
N,N-Diethyl 5-Nitronicotinamide
N-Ethyl-N-methyl 5-Nitronicotinamide
N-Acetyl 5-Nitronicotinamide
N-Propionyl 5-Nitronicotinamide
N-Butyryl 5-Nitronicotinamide
N-Isobutyryl 5-Nitronicotinamide
N-Valeryl 5-Nitronicotinamide
N-Isovaleryl 5-Nitronicotinamide
N-Pivaloyl 5-Nitronicotinamide
N-Hexanoyl 5-Nitronicotinamide
N-Octanoyl 5-Nitronicotinamide
N-Nonanoyl 5-Nitronicotinamide
N-Acryloyl 5-Nitronicotinamide
N-Crotonoyl 5-Nitronicotinamide
N-Benzoyl 5-Nitronicotinamide
N-(o-Toluoyl) 5-Nitronicotinamide
N-(m-Toluoyl) 5-Nitronicotinamide
N-(p-Toluoyl) 5-Nitronicotinamide
N-(p-Methoxybenzoyl) 5-Nitronicotinamide
N-(5-Nitronicotinoyl) 5-Nitronicotinamide
5-Nitronicotinohydroxamic acid
N-Methyl 2-Methyl-5-nitronicotinamide
N-Ethyl 2-Methyl-5-nitronicotinamide
N,N-Dimethyl 2-Methyl-5-nitronicotinamide
N,N-Diethyl 2-Methyl-5-nitronicotinamide
N-Ethyl-N-methyl 2-Methyl-5-nitronicotinamide
N-Acetyl 2-Methyl-5-nitronicotinamide
N-Propionyl 2-Methyl-5-nitronicotinamide
N-Butyryl 2-Methyl-5-nitronicotinamide
N-Isobutyryl 2-Methyl-5-nitronicotinamide
N-Valeryl 2-Methyl-5-nitronicotinamide
N-Isovaleryl 2-Methyl-5-nitronicotinamide
N-Pivaloyl 2-Methyl-5-nitronicotinamide
N-Hexanoyl 2-Methyl-5-nitronicotinamide
N-Octanoyl 2-Methyl-5-nitronicotinamide
N-Nonanoyl 2-Methyl-5-nitronicotinamide
N-Acryloyl 2-Methyl-5-nitronicotinamide
N-Crotonoyl 2-Methyl-5-nitronicotinamide
N-(3,4-Dimethylbenzoyl) 2-Methyl-5-nitronicotinamide
N-(o-Toluoyl) 2-Methyl-5-nitronicotinamide
N-(m-Toluoyl) 2-Methyl-5-nitronicotinamide N-(p-Toluoyl) 2-Methyl-5-nitronicotinamide
N-(p-Methoxybenzoyl) 2-Methyl-5-nitronicotinamide
2-Methyl-5-nitronicotinohydroxamic acid
N-Methyl 3-Nitroisonicotinamide
N-Ethyl 3-Nitroisonicotinamide
N,N-Dimethyl 3-Nitroisonicotinamide
N,N-Diethyl 3-Nitroisonicotinamide
N-Acetyl 3-Nitroisonicotinamide
N-Propionyl 3-Nitroisonicotinamide
N-Butyryl 3-Nitroisonicotinamide
N-Isobutyryl 3-Nitroisonicotinamide
N-Valeryl 3-Nitroisonicotinamide
N-Isovaleryl 3-Nitroisonicotinamide
N-Pivaroyl 3-Nitroisonicotinamide
N-Hexanoyl 3-Nitroisonicotinamide
N-Octanoyl 3-Nitroisonicotinamide
N-Crotonoyl 3-Nitroisonicotinamide
N-Benzoyl 3-Nitroisonicotinamide
N-(o-Toluoyl) 3-Nitroisonicotinamide
N-(m-Toluoyl) 3-Nitroisonicotinamide
N-(p-Toluoyl) 3-Nitroisonicotinamide and
N,N-Dimethyl 3-Nitro-2-pyridinecarboxamide.

8. The anticoccidial composition according to claim 1 wherein said compound is selected from the group consisting of 5-Nitronicotinamide
N-Methyl 5-Nitronicotinamide
N-Ethyl 5-Nitronicotinamide
N,N-Dimethyl 5-Nitronicotinamide
N-Ethyl-N-methyl 5-Nitronicotinamide
N-Acetyl 5-Nitronicotinamide
N-Valeryl 5-Nitronicotinamide
N-Octanoyl 5Nitronicotinamide
N-Crotonoyl 5-Nitronicotinamide
N-Benzoyl 5-Nitronicotinamide
N-(p-Toluoyl) 5-Nitronicotinamide
N-(p-Methoxybenzoyl) 5-Nitronicotinamide
N-(5-Nitronicotinoyl) 5-Nitronicotinamide
5-Nitronicotinohydroxamic acid
N-Ethyl 2-Methyl-5-nitronicotinamide
N,N-Diethyl 2-Methyl-5-nitronicotinamide
N-Ethyl-N-methyl 2-Methyl-5-nitronicotinamide
N-Acetyl 2-Methyl-5-nitronicotinamide
N-Propionyl 2-Methyl-5-nitronicotinamide
N-Isobutyryl 2-Methyl-5-nitronicotinamide
N-Pivaloyl 2-Methyl-5-nitronicotinamide
N-Octanoyl 2-Methyl-5-nitronicotinamide
N-Crotonoyl 2-Methyl-5-nitronicotinamide
N-(3,4-Dimethylbenzoyl) 2-Methyl-5-nitronicotinamide
2-Methyl-5-nitronicotinohydroxamic acid
N-Methyl 3-Nitroisonicotinamide
N,N-Dimethyl 3-Nitroisonicotinamide
N-Acetyl 3-Nitroisonicotinamide
N-Crotonoyl 3-Nitroisonicotinamide
N-Benzoyl 3-Nitroisonicotinamide and
N,N-Dimethyl 3-Nitro-2-pyridinecarboxamide.

9. A poultry feed having dispersed therein for control of poultry coccidiosis at least 0.005% by weight of a compound having the formula

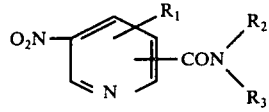

wherein
R₁ is hydrogen atom, a halomethyl group or methyl group;
R₂ is hydrogen atom or an alkyl group of 1-3 carbon atoms;
R₃ is hydrogen atom, an alkyl group of 1-3 carbon atoms, allyl group, an alkyl group having 2 to 3 carbon atoms and alkoxy of 1 or 2 carbon atoms as a substituent, an alkly group having 1-3 carbon atoms and hydroxy as a substituent, an alkanoyl group of 1-18 carbon atoms, a haloacetyl group, an alkenoyl group of 3-11 carbon atoms, an aromatic acyl group selected from the group consisting of benzoyl, 2,3-dimethoxybenzoyl, 3,4-dimethoxybenzoyl, 3,5-dimethoxybenzoyl, o-, m-, p-toluoyl, o-, m-, p-chlorobenzoyl, o-, m-, p-bromobenzoyl, p-methoxybenzoyl, o-, m-, p-acetylaminobenzoyl, o-, m-, p-cyanobenzoyl, 2-ethoxy-4-acetylaminobenzoyl, 2-ethoxy-4-dimethylaminobenzoyl, 2-methoxy-4-acetylaminobenzoyl, 3,5-dimethylbenzoyl, and 3,4-dimethylbenzoyl, a heterocyclic acyl group selected from the group consisting of 2-furoyl, 2-thenoyl, isonicotinoyl, nicotinoyl, 5-nitronicotinoyl, and 2-methyl-5-nitronicotinoyl, an N-alkylcarbamoyl group of 1-4 carbon atoms in the alkyl moiety or hydroxy group;
or an inorganic acid addition salt thereof;
provided that when R₂ is said alkyl group of 1-3 carbon atoms, R₃ is said alkyl group of 1-3 carbon atoms, and provided that the compound of formula (I) is not defined by a methyl group at the 6-position and a —COHN₂ group at the 5-position.

10. The poultry feed according to claim 9 wherein
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1-9 carbon atoms, chloroacetyl group, an alkenoyl group of 3 or 4 carbon atoms, a benzoyl group which may be substituted with methyl, methoxy or halogen, nicotinoyl group, 5-nitronicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

11. The poultry feed according to claim 9 wherein
R₁ is attached to the pyridine ring at the 6-position thereof and is hydrogen atom or methyl group, the

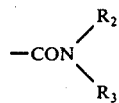

group is attached to the pyridine ring at the 3-position thereof and
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1-9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

12. The poultry feed according to claim 9 wherein
R₁ is attached to the pyridine ring at the 2-position thereof and is hydrogen atom or methyl group, the

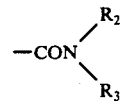

group is attached to the pyridine ring at the 4-position thereof and
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1-9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

13. The poultry feed according to claim 9 wherein
R₁ is hydrogen atom or methyl group, the

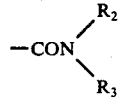

group is attached to the pyridine ring at the 2-position thereof and
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1-9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

14. The poultry feed according to claim 9 wherein $R_1$ is attached to the pyridine ring at the 2- or 4-position thereof and is hydrogen atom or methyl group, the

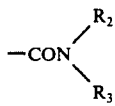

group is attached to the pyridine ring at the 2-position thereof and $R_2$ is hydrogen atom or an alkyl group of 1 or 2 carbon atoms;

$R_3$ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1-9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;

provided that when $R_2$ is said alkyl group, $R_3$ is said alkyl group of 1 or 2 carbon atoms.

15. The poultry feed according to claim 9 wherein said compound is selected from the group consisting of
5-Nitronicotinamide
N-Methyl 5-Nitronicotinamide
N-Ethyl 5-Nitronicotinamide
N,N-Dimethyl 5-Nitronicotinamide
N,N-Diethyl 5-Nitronicotinamide
N-Ethyl-N-methyl 5-Nitronicotinamide
N-Acetyl 5-Nitronicotinamide
N-Propionyl 5-Nitronicotinamide
N-Butyryl 5-Nitronicotinamide
N-Isobutyryl 5-Nitronicotinamide
N-Valeryl 5-Nitronicotinamide
N-Isovaleryl 5-Nitronicotinamide
N-Pivaloyl 5-Nitronicotinamide
N-Hexanoyl 5-Nitronicotinamide
N-Octanoyl 5-Nitronicotinamide
N-Nonanoyl 5-Nitronicotinamide
N-Acryloyl 5-Nitronicotinamide
N-Crotonoyl 5-Nitronicotinamide
N-Benzoyl 5-Nitronicotinamide
N-(o-Tolyoyl) 5-Nitronicotinamide
N-(m-Toluoyl) 5-Nitronicotinamide
N-(p-Toluoyl) 5-Nitronicotinamide
N-(p-Methoxybenzoyl) 5-Nitronicotinamide
N-(5-Nitronicotinoyl) 5-Nitronicotinamide
5-Nitronicotinohydroxamic acid
N-Methyl 2-Methyl-5-nitronicotinamide
N-Ethyl 2-Methyl-5-nitronicotinamide
N,N-Dimethyl 2-Methyl-5-nitronicotinamide
N,N-Diethyl 2-Methyl-5-nitronicotinamide
N-Ethyl-N-methyl 2-Methyl-5-nitronicotinamide
N-Acetyl 2-Methyl-5-nitronicotinamide
N-Propionyl 2-Methyl-5-nitronicotinamide
N-Butyryl 2-Methyl-5-nitronicotinamide
N-Isobutyryl 2-Methyl-5-nitronicotinamide
N-Valeryl 2-Methyl-5-nitronicotinamide
N-Isovaleryl 2-Methyl-5-nitronicotinamide
N-Pivaloyl 2-Methyl-5-nitronicotinamide
N-Hexanoyl 2-Methyl-5-nitronicotinamide
N-Octanoyl 2-Methyl-5-nitronicotinamide
N-Nonanoyl 2-Methyl-5-nitronicotinamide
N-Acryloyl 2-Methyl-5-nitronicotinamide
N-Crotonoyl 2-Methyl-5-nitronicotinamide
N-(3,4-Dimethylbenzoyl) 2-Methyl-5-nitronicotinamide
N-(o-Toluoyl) 2-Methyl-5-nitronicotinamide
N-(m-Toluoyl) 2-Methyl-5-nitronicotinamide
N-(p-Toluoyl) 2-Methyl-5-nitronicotinamide
N-(p-Methoxybenzoyl) 2-Methyl-5-nitronicotinamide
2-Methyl-5-nitronicotinohydroxamic acid
N-Methyl 3-Nitroisonicotinamide
N-Ethyl 3-Nitroisonicotinamide
N,N-Dimethyl 3-Nitroisonicotinamide
N,N-Diethyl 3-Nitroisonicotinamide
N-Acetyl 3-Nitroisonicotinamide
N-Propionyl 3-Nitroisonicotinamide
N-Butyryl 3-Nitroisonicotinamide
N-Isobutyryl 3-Nitroisonicotinamide
N-Valeryl 3-Nitroisonicotinamide
N-Isovaleryl 3-Nitroisonicotinamide
N-Pivaroyl 3-Nitroisonicotinamide
N-Hexanoyl 3-Nitroisonicotinamide
N-Octanoyl 3-Nitroisonicotinamide
N-Crotonoyl 3-Nitroisonicotinamide
N-Benzoyl 3-Nitroisonicotinamide
N-(o-Toluoyl) 3-Nitroisonicotinamide
N-(m-Toluoyl) 3-Nitroisonicotinamide
N-(p-Toluoyl) 3-Nitroisonicotinamide and
N,N-Dimethyl 3-Nitro-2-pyridinecarboxamide.

16. The poultry feed according to claim 9 wherein said compound is selected from the group consisting of
5-Nitronicotinamide
N-methyl 5-Nitronicotinamide
N-Ethyl 5-Nitronicotinamide
N,N-Dimethyl 5-Nitronicotinamide
N-Ethyl-N-methyl 5-Nitronicotinamide
N-Acetyl 5-Nitronicotinamide
N-Valeryl 5-Nitronicotinamide
N-Octanoyl 5-Nitronicotinamide
N-Crotonoyl 5-Nitronicotinamide
N-Benzoyl 5-Nitronicotinamide
N-(p-Toluoyl) 5-Nitronicotinamide
N-(p-Methoxybenzoyl) 5-Nitronicotinamide
N-(5-Nitronicotinoyl) 5-Nitronicotinamide
5-Nitronicotinohydroxamic acid
N-Ethyl 2-Methyl-5-nitronicotinamide
N,N-Diethyl 2-Methyl-5-nitronicotinamide
N-Ethyl-N-methyl 2-Methyl-5-nitronicotinamide
N-Acetyl 2-Methyl-5-nitronicotinamide
N-Propionyl 2-Methyl-5-nitronicotinamide
N-Isobutyryl 2-Methyl-5-nitronicotinamide
N-Pivaloyl 2-Methyl-5-nitronicotinamide
N-Octanoyl 2-Methyl-5-nitronicotinamide
N-Crotonoyl 2-Methyl-5-nitronicotinamide
N-(3,4-Dimethylbenzoyl) 2-Methyl-5-nitronicotinamide
2-Methyl-5-nitronicotinohydroxamic acid
N-Methyl 3-Nitroisonicotinamide
N,N-Dimethyl 3-Nitroisonicotinamide
N-Acetyl 3-Nitroisonicotinamide
N-Crotonoyl 3-Nitroisonicotinamide
N-Benzoyl 3-Nitroisonicotinamide and
N,N-Dimethyl 3-Nitro-2-pyridinecarboxamide.

17. A method of controlling poultry coccidiosis which comprises orally administering to poultry susceptible to coccidiosis an anticoccidial amount of a compound having the formula

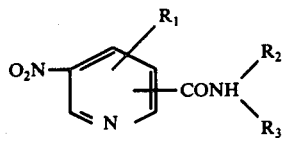 (I)

wherein
R₁ is hydrogen atom, a halomethyl group or methyl group;
R₂ is hydrogen atom or an alkyl group of 1-3 carbon atoms;
R₃ is hydrogen atom, an alkyl group of 1-3 carbon atoms, allyl group, an alkyl group having 2 or 3 carbon atoms and alkoxy of 1 or 2 carbon atoms as a substituent, an alkyl group having 1-3 carbon atoms and hydroxy as a substituent, an alkanoyl group of 1-18 carbon atoms, a haloacetyl group, an alkenoyl group of 3-11 carbon atoms, an aromatic acyl group selected from the group consisting of benzoyl, 2,3-dimethoxybenzoyl, 3,4-dimethoxybenzoyl, 3,5-dimethoxybenzoyl, o-, m-, p-toluoyl, o-, m-, p-chlorobenzoyl, o-, m-, p-bromobenzoyl, p-methoxybenzoyl, o-, m-, p-acetylaminobenzoyl, o-, m-, p-cyanobenzoyl, 2-ethoxy-4-acetylaminobenzoyl, 2-ethoxy-4-diemthylaminobenzoyl, 2-methoxy-4-acetylaminobenzoyl, 3,5-dimethylbenzoyl, and 3,4-dimethylbenzoyl, a heterocyclic acyl group selected from the group consisting of 2-furoyl, 2-thenoyl, isonicotinoyl, nicotinoyl, 5-nitronicotinoyl, and 2-methyl-5-nitronicotinoyl, an N-alkylcarbamoyl group of 1-4 carbon atoms in the alkyl moiety or hydroxy group;
or an inorganic acid addition salt thereof;
provided that when R₂ is said alkyl group of 1-3 carbon atoms, R₃ is said alkyl group of 1-3 carbon atoms and provided that the compound of formula (I) is not defined by a methyl group at the 6-position and a —CONH₂ group at the 5-position.

18. The method according to claim 17 wherein
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1 - 9 carbon atoms, chloroacetyl group, an alkenoyl group of 3 or 4 carbon atoms, a benzoyl group which may be substituted with methyl, methoxy or halogen, nicotinoyl group, 5-nitronicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

19. The method according to claim 17 wherein
R₁ is attached to the pyridine ring at the 6-position thereof and is hydrogen atom or methyl group, the

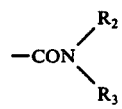

group is attached to the pyridine ring at the 3-position thereof and
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1 - 9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

20. The method according to claim 17 wherein
R₁ is attached to the pyridine ring at the 2-position thereof and is hydrogen atom or methyl group, the

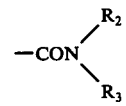

group is attached to the pyridine ring at the 4-position thereof and
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1 - 9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

21. The method according to claim 17 wherein
R₁ is hydrogen atom or methyl group, the

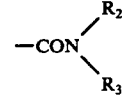

group is attached to the pyridine ring at the 2-position thereof and
R₂ is hydrogen atom or an alkyl group of 1 or 2 carbon atoms;
R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1 - 9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;
provided that when R₂ is said alkyl group, R₃ is said alkyl group of 1 or 2 carbon atoms.

22. The method according to claim 17 wherein

R₁ is attached to the pyridine ring at the 2- or 4-position thereof and is hydrogen atom or methyl group, the

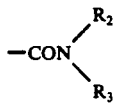

group is attached to the pyridine ring at the 2-position thereof and

R₂ is hydrogen atom or an alkyl group of 1 or 2 carbon atoms;

R₃ is hydrogen atom, an alkyl group of 1 or 2 carbon atoms, allyl group, an alkoxyethyl group of 1 or 2 carbon atoms in the alkoxy moiety, a hydroxyalkyl group of 1 or 2 carbon atoms, an alkanoyl group of 1 - 9 carbon atoms, an alkenoyl group of 3 or 4 carbon atoms, a benzoyl group which may be substituted with methyl, methoxy or halogen, nicotinoyl group, 2-thenoyl group, an N-alkylcarbamoyl group of 1 or 2 carbon atoms in the alkyl moiety or hydroxy group;

provided that when R₂ is said alkyl group, R₃ is said alkyl group of 1 or 2 carbon atoms.

23. The method according to claim 17 wherein said compound is selected from the group consisting of
5-Nitronicotinamide
N-Methyl 5-Nitronicotinamide
N-Ethyl 5-Nitronicotinamide
N,N-Dimethyl 5-Nitronicotinamide
N,N-Diethyl 5-Nitronicotinamide
N-Ethyl-N-methyl 5-Nitronicotinamide
N-Acetyl 5-Nitronicotinamide
N-Propionyl 5-Nitronicotinamide
N-Butyryl 5-Nitronicotinamide
N-Isobutyryl 5-Nitronicotinamide
N-Valeryl 5-Nitronicotinamide
N-Isovaleryl 5-Nitronicotinamide
N-Pivaloyl 5-Nitronicotinamide
N-Hexanoyl 5-Nitronicotinamide
N-Octanoyl 5-Nitronicotinamide
N-Nonanoyl 5-Nitronicotinamide
N-Acryloyl 5-Nitronicotinamide
N-Crotonoyl 5-Nitronicotinamide
N-Benzoyl 5-Nitronicotinamide
N-(o-Toluoyl) 5-Nitronicotinamide
N-(m-Toluoyl) 5-Nitronicotinamide
N-(p-Toluoyl) 5-Nitronicotinamide
N-(p-Methoxybenzoyl) 5-Nitronicotinamide
N-(5-Nitronicotinoyl) 5-Nitronicotinamide
5-Nitronicotinohydroxamic acid
N-Methyl 2-Methyl-5-nitronicotinamide
N-Ethyl 2-Methyl-5-nitronicotinamide
N,N-Dimethyl 2-Methyl-5-nitronicotinamide
N,N-Diethyl 2-methyl-5-nitronicotinamide
N-Ethyl-N-methyl 2-Methyl-5-nitronicotinamide
N-Acetyl 2-Methyl-5-nitronicotinamide
N-Propionyl 2-Methyl-5-nitronicotinamide
N-Butyryl 2-Methyl-5-nitronicotinamide
N-Isobutyryl 2-Methyl-5-nitronicotinamide
N-Valeryl 2-methyl-5-nitronicotinamide
N-Isovaleryl 2-Methyl-5-nitronicotinamide
N-Pivaloyl 2-Methyl-5-nitronicotinamide
N-Hexanoyl 2-Methyl-5-nitronicotinamide
N-Octanoyl 2-Methyl-5-nitronicotinamide
N-Nonanoyl 2-methyl-5-nitronicotinamide
N-Acryloyl 2-Methyl-5-nitronicotinamide
N-Crotonoyl 2-Methyl-5-nitronicotinamide
N-(3,4-Dimethylbenzoyl) 2-Methyl-5-nitronicotinamide
N-(o-Toluoyl) 2-Methyl-5-nitronicotinamide
N-(m-Toluoyl) 2-Methyl-5-nitronicotinamide
N-(p-Toluoyl) 2-Methyl-5-nitronicotinamide
N-(p-Methoxybenzoyl) 2-Methyl-5-nitronicotinamide
2-Methyl-5-nitronicotinohydroxamic acid
N-methyl 3-Nitroisonicotinamide
N-Ethyl 3-Nitroisonicotinamide
N,N-Dimethyl 3-Nitroisonicotinamide
N,N-Diethyl 3-Nitroisonicotinamide
N-Acetyl 3-Nitroisonicotinamide
N-Propionyl 3-Nitroisonicotinamide
N-Butyryl 3-Nitroisonicotinamide
N-Isobutyryl 3-Nitroisonicotinamide
N-Valeryl 3-Nitroisonicotinamide
N-Isovaleryl 3-Nitroisonicotinamide
N-Pivaroyl 3-Nitroisonicotinamide
N-Hexanoyl 3-Nitroisonicotinamide N-Octanoyl 3-Nitroisonicotinamide
N-Crotonoyl 3-Nitroisonicotinamide
N-Benzoyl 3-Nitroisonicotinamide
N-(o-Toluoyl) 3-Nitroisonicotinamide
N-(m-Toluoyl) 3-Nitroisonicotinamide
N-(p-Toluoyl) 3-Nitroisonicotinamide and
N,N-Dimethyl 3-Nitro-2-pyridinecarboxamide.

24. The method according to claim 17 wherein said compound is selected from the group consisting of
5-Nitronicotinamide
N-Methyl 5-Nitronicotinamide
N-Ethyl 5-Nitronicotinamide
N,N-Dimethyl 5-Nitronicotinamide
N-Ethyl-N-methyl 5-Nitronicotinamide
N-Acetyl 5-Nitronicotinamide
N-Valeryl 5-Nitronicotinamide
N-Octanoyl 5-Nitronicotinamide
N-Crotonoyl 5-Nitronicotinamide
N-Benzoyl 5-Nitronicotinamide
N-(p-Toluoyl) 5-nitronicotinamide
N-(p-Methoxybenzoyl) 5-Nitronicotinamide
N-(5-Nitronicotinoyl) 5-Nitronicotinamide
5-Nitronicotinohydroxamic acid
N-Ethyl 2-Methyl-5-nitronicotinamide
N,N-Diethyl 2-Methyl-5-nitronicotinamide
N-Ethyl-N-methyl 2-Methyl-5-nitronicotinamide
N-Acetyl 2-Methyl-5-nitronicotinamide
N-Propionyl 2-Methyl-5-nitronicotinamide
N-Isobutyryl 2-Methyl-5-nitronicotinamide
N-Pivaloyl 2-Methyl-5-nitronicotinamide
N-Octanoyl 2-Methyl-5-nitronicotinamide
N-Crotonoyl 2-Methyl-5-nitronicotinamide
N-(3,4-Dimethylbenzoyl) 2-Methyl-5-nitronicotinamide
2-Methyl-5-nitronicotinohydroxamic acid
N-Methyl 3-Nitroisonicotinamide
N,N-Dimethyl 3-Nitroisonicotinamide
N-Acetyl 3-Nitroisonicotinamide
N-Crotonoyl 3-Nitroisonicotinamide
N-Benzoyl 3-Nitroisonicotinamide and
N,N-Dimethyl 3-Nitro-2-pyridinecarboxamide.

25. A method of controlling poultry coccidiosis which comprises orally administering an anticoccidial amount of 2-methyl-5-nitronicotinamide to poultry susceptible to coccidiosis and which has not been deliberately inoculated with protozoa causing coccidiosis.

26. A method of controlling poultry coccidiosis of poultry susceptible to coccidiosis and which have been inoculated with 42,000 occysts of protozoa consisting of *Eimeria tenella*, which comprises orally administering to said poultry an anticoccidial amount of 2-methyl-5-nitronicotinamide.

* * * * *

UNITED STATES PATENT AND TRADEMARK OFFICE
CERTIFICATE OF CORRECTION

PATENT NO. : 4,053,608
DATED : October 11, 1977
INVENTOR(S) : YASUHIRO MORISAWA et al It is certified that error appears in the above-identified patent and that said Letters Patent are hereby corrected as shown below:

Column 1, line 51: before "chemotherapeutic", replace "is" with ---in---.

Column 3, line 8: replace "O-" with --- o- ---.

Column 4, lines 59-60: replace "anticoccidialactivity" with ---anticoccidial activity---.

Column 6, at "(160)": before "Bromomethyl", insert --- 2- ---.

Column 8, at "(256)", "(257)" and "(258)": after "Toluoyl", insert ---)---;

at "(259)" and "(260)": after "-benzoyl", insert ---)---.

Columns 11-12, in formula (XVII): replace

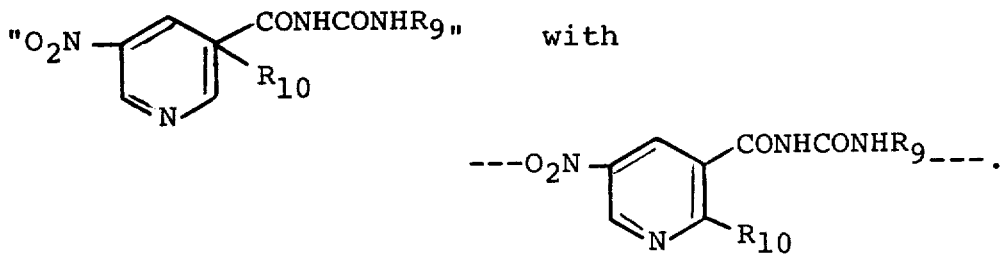

UNITED STATES PATENT AND TRADEMARK OFFICE
CERTIFICATE OF CORRECTION

PATENT NO. : 4,053,608
DATED : October 11, 1977
INVENTOR(S) : YASUHIRO MORISAWA et al It is certified that error appears in the above-identified patent and that said Letters Patent are hereby corrected as shown below:

Column 17, line 1: replace "5nitronicotinamide" with ---5-nitronicotinamide---.

Column 23, Claim 1, formula I: insert numeral ---6--- to the ring (see numerals 1 through 5 which have been correctly printed around the ring).

Column 23, line 48 (Claim 2): after "group", replace "or" with ---of---.

Column 23, line 59 (Claim 3): rewrite "wheren" as ---wherein---.

Column 26, lines 11-12 (Claim 7): print the compound "N-(p-Toluoyl)..." on one separate line.

Column 26, line 44 (Claim 8): replace "5Nitronicotinamide" with ---5-Nitronicotinamide---.

Column 27, line 19 (Claim 9): rewrite "alkly" as ---alkyl---.

Column 27, line 42 (Claim 9): replace "-COHN$_2$" with --- -CONH$_2$---.

UNITED STATES PATENT AND TRADEMARK OFFICE
CERTIFICATE OF CORRECTION

PATENT NO. : 4,053,608

DATED : October 11, 1977

INVENTOR(S) : YASUHIRO MORISAWA et al

It is certified that error appears in the above-identified patent and that said Letters Patent are hereby corrected as shown below:

Column 29, line 47 (Claim 15): replace "Tolyoyl" with ---Toluoyl---.

Column 31, line 27 (Claim 17): replace "diemthylamino-benzoyl" with ---dimethylaminobenzoyl---.

Column 34, lines 18-19 (Claim 23): print the compound "N-Octanoyl 3-Nitroisonicotinamide" on one separate line.

Signed and Sealed this

Eleventh Day of July 1978

[SEAL]

Attest:

RUTH C. MASON
*Attesting Officer*

DONALD W. BANNER
*Commissioner of Patents and Trademarks*